(12) United States Patent
Ogidigben et al.

(10) Patent No.: US 7,279,490 B2
(45) Date of Patent: Oct. 9, 2007

(54) OPHTHALMIC COMPOSITIONS FOR TREATING OCULAR HYPERTENSION

(75) Inventors: Miller J Ogidigben, Schwenksville, PA (US); Takeru Yamakawa, Tsukuba (JP); Yufu Sagara, Tsukuba (JP)

(73) Assignee: Merck & Co, Inc., Rahway, NJ (US)

( * ) Notice: Subject to any disclaimer, the term of this patent is extended or adjusted under 35 U.S.C. 154(b) by 265 days.

(21) Appl. No.: 10/515,127

(22) PCT Filed: Jun. 17, 2003

(86) PCT No.: PCT/US03/19263

§ 371 (c)(1),
(2), (4) Date: Nov. 18, 2004

(87) PCT Pub. No.: WO03/105781

PCT Pub. Date: Dec. 24, 2003

(65) Prior Publication Data

US 2005/0176765 A1 Aug. 11, 2005

Related U.S. Application Data

(60) Provisional application No. 60/389,220, filed on Jun. 17, 2002.

(51) Int. Cl.
*A61K 31/4545* (2006.01)
*C07D 401/14* (2006.01)

(52) U.S. Cl. .................. 514/316; 546/187

(58) Field of Classification Search ............ 514/316, 514/322; 546/187
See application file for complete search history.

(56) References Cited

U.S. PATENT DOCUMENTS

| | | |
|---|---|---|
| 4,386,098 A | 5/1983 | Woltersdorf, Jr. |
| 4,416,890 A | 11/1983 | Woltersdorf, Jr. |
| 4,426,388 A | 1/1984 | Woltersdorf, Jr. |
| 4,599,353 A | 7/1986 | Bito |
| 4,668,697 A | 5/1987 | Shepard et al. |
| 4,797,413 A | 1/1989 | Baldwin et al. |
| 4,824,857 A | 4/1989 | Goh et al. |
| 4,863,922 A | 9/1989 | Baldwin et al. |
| 4,883,819 A | 11/1989 | Bito |
| 5,001,153 A | 3/1991 | Ueno et al. |
| 5,153,192 A | 10/1992 | Dean et al. |
| 5,240,923 A | 8/1993 | Dean et al. |
| 5,378,703 A | 1/1995 | Dean et al. |
| 5,574,044 A * | 11/1996 | Thompson et al. .......... 514/316 |
| 5,718,912 A | 2/1998 | Thomspon et al. |
| 5,756,508 A | 5/1998 | Thompson et al. |

FOREIGN PATENT DOCUMENTS

| | | |
|---|---|---|
| JP | 10330377 | 12/1998 |
| WO | WO96/13262 | 5/1996 |
| WO | WO97/16186 | 5/1997 |
| WO | WO97/16192 | 5/1997 |
| WO | WO97/24324 | 7/1997 |
| WO | WO99/32481 | 7/1999 |
| WO | WO 01/27104 | 4/2001 |
| WO | WO01/30348 | 5/2001 |

OTHER PUBLICATIONS

Gil, et al., Investigative Opthalmology & Visual Science, "Muscarinic Receptor Subtypes in Human Iris—Ciliary Body Measured by Immunoprecipitation", (1997), vol. 38 No. 7, pp. 1437-1442.

Ward, et al., J. Med. Chem., 1,2,5-Thiadiazole Analogues of Aceclidine as Potent m1 Muscarinic Agonists, (1998), vol. 41, pp. 379-392.

Sauerbert, et al., Bioorganic & Medicinal Chemistry Letter 8, "Identification of Side Chains on 1,2,5,-Thiadiazole-Azacycles Optimal for Muscarinic M1 Receptor Activation", (1998), pp. 2897-2902.

Berge, et al., Journal of Pharmaceutical Sciences, "Pharmaceutical Salts", (1977), vol. 66, No. 1, pp. 1-19.

Jeppesen, et al., J. Med. Chem., 1-(1,2,5-Thiadiazol-4-yl)-4-azatricyclo[2.2.1.02,6] heptanes as New Potent Muscarinic . . . (1998), vol. 42, pp. 1999-2006.

Robert A. Schumer, Arch. Opthalmol, "The Nerve of Glaucoma", (1994), vol. 112, pp. 37-44.

Dandona, et al., Invest. Ophthalmol. Vis. Sci., "Selective Effects of Experimental Glaucoma on Axonal Transport by Retinal anglion Cells to the Dorsal Lateral Geniculate Nucleus", (1991), vol. 32, No. 5, pp. 1593-1599.

Eliel, et al., Stereochemistry of Organic Compounds, (1994), 14:1, pp. 1119-1190.

Bonner, et al., Science, "Identification of a Family of Muscarinic Acetylcholine Receptor Genes", (1987), vol. 237, pp. 527-532.

* cited by examiner

*Primary Examiner*—Charanjit S. Aulakh
(74) *Attorney, Agent, or Firm*—Sylvia A. Ayler; William Krovatin

(57) ABSTRACT

This invention relates to selective m1 muscarinic agonist, their use or a formulation thereof in the treatment of glaucoma and/or other conditions which are related to elevated intraocular pressure in the eye of a patient. This invention also relates to the use of such compounds to provide a neuroprotective effect to the eye of mammalian species, particularly humans. In addition, the present invention relates to the use of the compounds in the treatment of dementia such as Alzheimer's disease and vascular dementia, depression, attention deficit disorder, sleep disorder, schizophrenia, pain, ischemia, atrophic gastritis, and atony of gastrointestinal tract.

15 Claims, No Drawings

US 7,279,490 B2

OPHTHALMIC COMPOSITIONS FOR TREATING OCULAR HYPERTENSION

CROSS REFERENCE TO RELATED APPLICATIONS

This application is the National Stage of International Application No. PCT/US03/19263 filed on Jun. 17, 2003 which claims the benefit under 35 U.S.C. 119(e) of U.S. Provisional Application No. 60/389,220 filed on Jun. 17, 2002.

BACKGROUND OF THE INVENTION

Glaucoma is a degenerative disease of the eye comprising a group of eye diseases, usually associated with an increase in intraocular pressure due to an imbalance in aqueous humor dynamics. Open-angle glaucoma is the most common form of glaucoma in the western world and is characterized by deficient drainage of aqueous humor, and normal or increased intraocular pressure (IOP). The pathological changes that occur in the optic nerve head, the optic disk (degeneration of the retinal ganglion cells) result in loss of vision and eventual blindness.

Many of the drugs formerly used to treat glaucoma proved unsatisfactory. Early methods of treating glaucoma employed pilocarpine, a non-selective muscarinic agonist, and/or epinephrine. These agents decrease resistance to aqueous humor flow in the traecular meshwork outflow channels that represent 85 to 90% of aqueous outflow in the eye. However, pilocarpine and epinephrine produce undesirable local effects that made these drugs, though valuable, unsatisfactory as a first line drug. For a discussion on m1 receptor agonists see D. W. Gil, et al., *Invest-Ophthalmol, Vis. Sci.* 1997 June; 38(7): 1434-42; J. S. Ward et al., *J. Med. Chem.* 1998 Jan. 29; 41(3): 379-92; Sauerbert, et al., *Bioorg. Med. Chem Let.* 1998, 8: 2897-2902; and L. Jeppesen, *J. Med. Chem.* 1999 June 3; 42(11): 1999-2006.

More recently, clinicians have noted that many β-adrenergic antagonists are effective in reducing intraocular pressure. While many of these agents are effective for this purpose, there exist some patients in whom this treatment is not effective or not sufficiently effective. Many of these agents also have other characteristics, e.g., membrane stabilizing activity, that become more apparent with increased doses and render them unacceptable for chronic ocular use and can also cause cardiovascular effects. Alpha2 adrenergic receptor agonists such as clonidine and brimonidine are also agents used to treat elevated IOP.

Agents referred to as carbonic anhydrase inhibitors are also used to treat elevated IOP. They do so by decreasing the formation of aqueous humor by inhibiting the enzyme carbonic anhydrase. While such carbonic anhydrase inhibitors are now used to treat intraocular pressure by systemic and topical routes, current therapies using these agents, particularly those using systemic routes are still not without undesirable effects. Because carbonic anhydrase inhibitors have a profound effect in altering basic physiological processes, the avoidance of a systemic route of administration serves to diminish, if not entirely eliminate, those side effects caused by inhibition of carbonic anhydrase such as metabolic acidosis, vomiting, numbness, tingling, general malaise and the like. Topically effective carbonic anhydrase inhibitors are disclosed in U.S. Pat. Nos. 4,386,098; 4,416, 890; 4,426,388; 4,668,697; 4,863,922; 4,797,413; 5,378, 703, 5,240,923 and 5,153,192.

Prostaglandins and prostaglandin derivatives are also known to lower intraocular pressure. U.S. Pat. No. 4,883, 819 to Bito describes the use and synthesis of PGAs, PGBs and POCs in reducing intraocular pressure. U.S. Pat. No. 4,824,857 to Goh et al. describes the use and synthesis of PGD2 and derivatives thereof in lowering intraocular pressure including derivatives wherein C-10 is replaced with nitrogen. U.S. Pat. No. 5,001,153 to Ueno et al. describes the use and synthesis of 13,14-dihydro-15-keto prostaglandins and prostaglandin derivatives to lower intraocular pressure. U.S. Pat. No. 4,599,353 describes the use of eicosanoids and eicosanoid derivatives including prostaglandins and prostaglandin inhibitors in lowering intraocular pressure.

Prostaglandin and prostaglandin derivatives lower intraocular pressure by increasing uveoscleral outflow. This is true for both the F type and A type of PGs and hence presumably also for the B, C, D, E and J types of prostaglandins and derivatives thereof. A problem with using prostaglandin derivatives to lower intraocular pressure is that these compounds often induce an initial increase in intraocular pressure, can change the color of eye pigmentation and cause proliferation of some tissues surrounding the eye.

As can be seen, there are several current therapies for treating glaucoma and elevated intraocular pressure, but the efficacy and the side effect profiles of these agents are not ideal.

Intraocular pressure is determined by the rate of aqueous humor production and the resistance to aqueous humor outflow. This invention relates to novel muscarinic agonists that are selective for m1 receptors and their use to reduce intraocular pressure in the eye and therefore provide yet one more approach to the treatment of ocular hypertension and the degenerative ocular conditions related thereto. The m1 agonists decrease resistance of the structures of the limbus, such as the trabecular meshwork. Use of the selective m1 muscarinic agonist reduces or eliminates side effects elicited by alpha2 adrenergic agonists, beta adrenergic antagonists, potassium channel blockers, and prostaglandin analogs.

This invention also relates to use of the m1 agonists for the treatment of dementia such as Alzheimer's disease and vascular dementia, depression, attention deficit disorder, sleep disorder, schizophrenia, pain, atrophic gastritis, and atony of gastrointestinal tract.

Patent publications WO 97/24324 and WO 01/30348 disclose compounds structurally related to those of the present invention as tachykinin/Substance P antagonists, but these compounds are different from this invention in their pharmacological properties and structures.

Patent publications WO 96/13262, WO 97/16192 and U.S. Pat. No. 5,756,508 also disclose compounds analogous to the present invention as muscarinic antagonists. However, these prior art publications do not teach anything about the muscarinic agonist activity at all.

Patent publications WO 99/32481, WO 01/27104, WO 97/16186 and U.S. Pat. No. 5,718,912 disclose benzimidazolidinone derivatives as muscarinic agonists. However, these publications do not claim that their compounds show a m1 selectivity, neither do they contain any specific disclosure about the compounds of the present invention.

SUMMARY OF THE INVENTION

This invention relates to selective m1 muscarinic agonist, their use or a formulation thereof in the treatment of glaucoma and/or other conditions that are related to elevated intraocular pressure in the eye of a patient. This invention also relates to the use of such compounds to provide a neuroprotective effect to the eye of mammalian species, particularly humans. In addition, the present invention relates to the use of the compounds in the treatment of dementia such as Alzheimer's disease and vascular dementia, depression, attention deficit disorder, sleep disorder, schizophrenia, pain, ischemia, atrophic gastritis, and atony of gastrointestinal tract.

More particularly this invention relates to the treatment of glaucoma and/or ocular hypertension (elevated intraocular pressure) using novel selective m1 muscarinic agonist having the structural formula I:

FORMULA I

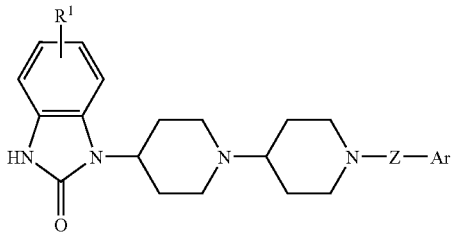

or a pharmaceutically acceptable salt, enantiomer, diastereomer or mixture thereof:

wherein, $R^1$ represents R, $R^8$, $(CH_2)_nOR$, $(CH_2)_nOR^8$, COOR, $COOR^8$, $(CH_2)_nN(R)_2$, $(CH_2)_nN(R)(R^8)$, $(CH_2)_nN^+(R)_3$, $(CH_2)_nNRCOR$, $(CH_2)_nN(R^8)CO_2R$, $(CH_2)_nN(R^8)COR$, $(CH_2)_nNRCO_2R$, $SO_2R$, $SO_2N(R)_2$, $(CH_2)_nCON(R)_2$, $CONRR^8$, $CONHC(R)_3$, COR, $COR^8$, $CON(R^8)_2$, nitro, cyano, or halogen, alkyl or alkoxy optionally substituted with 1-3 groups of $R^a$;

Z represents $CH_2$, CO, $CHCO_2R$, or $SO_2$;

Ar represents $(CH_2)_{n\ 5\text{-}11}$ heterocyclyl, $(CH_2)_nC_{5\text{-}10}$ heteroaryl, or $(CH_2)_nC_{6\text{-}10}$ aryl, said heterocycle, aryl or heteroaryl optionally substituted with 1-3 groups of $R^a$;

$R^a$ represents $C_1$-$C_6$ alkyl optionally substituted with fluoro, $C_{2\text{-}6}$ alkenyl, $C_{2\text{-}6}$ alkynyl, F, Cl, I, Br, $(CH_2)_nNR_2$, $(CH_2)_nNRR^8$, $NO_2$, CN, —$CF_3$, —COR, —$COR^8$, —$CONRR^8$, —$CONR_2$, —$(CH_2)_nCOOR$, —$(CH_2)_nNHCOR$, —$(CH_2)_nNHCOR^8$, —$(CH_2)_nNHCOOR$, —$SO_2NR_2$, —$SiR_3$, —$(CH_2)_nOR$, —$(CH_2)_nOR^8$, —$O(CH_2)OR$, —$(CH_2)_nO(CH_2)_nOR$, —$S(O)_mR$, —$S(O)_mR^8$, —$C(NH)NH_2$, $R^8$ R represents hydrogen, $C_{1\text{-}6}$ alkyl optionally substituted with fluoro, $C_{2\text{-}6}$ alkenyl, or C2-6 alkynyl;

$R^8$ represents $(CH_2)_nC_{3\text{-}8}$ cycloalkyl, $(CH_2)_nC_{5\text{-}11}$ heterocycle, $(CH_2)_nC_{5\text{-}10}$ heteroaryl, $(CH_2)_nC_{6\text{-}10}$ aryl, said heterocycle, aryl or heteroaryl optionally substituted with 1-3 groups of $R^b$;

$R^b$ represents F, Cl, I, Br, or $C_{1\text{-}6}$ alkyl n is 0-3 m is 0-2.

This and other aspects of the invention will be realized upon inspection of the invention as a whole.

DETAILED DESCRIPTION OF THE INVENTION

The present invention is directed to novel selective m1 muscarinic agonist of Formula I. It also relates to a method for decreasing elevated intraocular pressure or treating glaucoma by administration, preferably topical or intraocular injections such as intra-cameral administration, of a composition containing a selective m1 muscarinic agonist of Formula I and a pharmaceutically acceptable carrier. It also relates to a method for treating dementia such as Alzheimer's disease and vascular dementia, depression, attention deficit disorder, sleep disorder, schizophrenia, pain, ischemia, atrophic gastritis, and atony of gastrointestinal tract by administration, preferably oral, transdermal or intravenous administration, of the composition containing a selective m1 muscarinic agonist of Formula I and a pharmaceutically acceptable carrier.

One embodiment of this invention is realized when Z is $CH_2$ and all other variables are as originally described.

Another embodiment of this invention is realized when Z is CO and all other variables are as originally described.

Still another embodiment of this invention is realized when Ar is $(CH_2)_nC_{6\text{-}10}$ aryl and all other variables are as originally described. A subembodiment of this invention is realized when Ar is $(CH_2)_nC_{6\text{-}10}$ aryl optionally substituted with 1-2 groups of $R^a$ and n=0. A further subembodiment of this invention is realized when Z is CO, or $CH_2$.

Still another embodiment of this invention is realized when Ar is $(CH_2)_nC_{5\text{-}10}$ heteroaryl, and all other variables are as originally described. A subembodiment of this invention is realized when Ar is $(CH_2)_nC_{5\text{-}10}$ heteroaryl optionally substituted with 1-2 groups of $R^a$ and n=0. A further subembodiment of this invention is realized when Z is CO or $CH_2$.

Compounds to be used in this invention are:

1-[1-[1-(3-Thienoyl)piperidin-4-yl]piperidin-4yl]-1,3-dihydro-2H-benzimidazol-2-one;

1-[1-[1-(2-Methoxynicotinoyl)piperidin-4-yl]piperidin-4-yl]-1,3-dihydro-2H-benzimidazol-2-one;

1-[1-[1-[2-(Methoxycarbonyl)benzoyl]piperidin-4-yl]piperidin-4yl]-1,3-dihydro-2H-benzimidazol-2-one;

1-[1-[1-(2-Methoxybenzoyl)piperidin-4-yl]piperidin-4yl]-1,3-dihydro-2H-benzimidazol-2-one;

1-[1-[1-(4Methoxy-3-thenoyl)piperidin-4-yl]piperidin-4-yl]-1,3-dihydro-2H-benzimidazol-2-one;

1-[1-[1-[(1-Methyl-2-pyrrolyl)carbonyl]piperidin-4-yl]piperidin-4-yl]-1,3-dihydro-2H-benzimidazol-2-one;

1-[1-[1-[(3-Indolyl)carbonyl]piperidin-4-yl]piperidin-4-yl]-1,3-dihydro-2H-benzimidazol-2-one;

1-[1-[1-(2-Methylbenzoyl)piperidin-4-yl]piperidin-4-yl]-1,3-dihydro-2H-benzimidazol-2-one;

1-[1-[1-[2-(Methylthio)nicotinoyl]piperidin-4-yl]piperidin-4yl]-1,3-dihydro-2H-benzimidazol-2-one;

1-[1-[1-[2-(Methylthio)benzoyl]piperidin-4-yl]piperidin-4-yl]-1,3-dihydro-2H-benzimidazol-2-one;

1-[1-[1-[(1,2-Dihydro-1-benzofuran-7-yl)carbonyl]piperidin-4-yl]piperidin-4-yl]-1,3-dihydro-2H-benzimidazol-2-one;

1-[1-[1-(3-Chloro-2-thenoyl)piperidin-4-yl]piperidin-4-yl]-1,3-dihydro-2H-benzimidazol-2-one;

1-[1-[1-(2-Ethylbenzoyl)piperidin-4-yl]piperidin-4-yl]-1,3-dihydro-2H-benzimidazol-2-one;

1-[1-[1-[2-(Phenoxymethyl)benzoyl]piperidin-4-yl]piperidin-4-yl]-1,3-dihydro-2H-benzimidazol-2-one;

1-[1-[1-(3-Ethoxy-2-thenoyl)piperidin-4yl]piperidin-4yl]-1,3-dihydro-2H-benzimidazol-2-one;

1-[1-[1-(3-Methoxy-2-thenoyl)piperidin-4-yl]piperidin-4-yl]-1,3-dihydro-2H-benzimidazol-2-one;

1-[1-[1-(2-Methylbenzyl)piperidin-4-yl]piperidin-4-yl]-1,3-dihydro-2H-benzimidazol-2-one;

1-[1-[1-(2,6-Dimethylbenzyl)piperdin-4-yl]piperidin-4-]-1,3dihydro-2H-benzimidazol-2-one;

1-[1-[1-(2Chlorobenzyl)piperidin-4-yl]piperidin-4-yl]-1,3-dihydro-2H-benzimidazol-2-one;

1-[1-[1-[2-(Trifluoromethyl)benzyl]piperidin-4-yl]piperidin-4-yl]-1,3-dihydro-2H-benzimidazol-2-one;

1-[1-[1-(2-Thienylmethyl)piperidin-4-yl]piperidin-4-yl]-1,3-dihydro-2H-benzimidazol-2-one;

1-[1-[1-[2-(Methylthio)benzyl]piperidin-4-yl]piperidin-4-yl]-1,3-dihydro-2H-benzimidazol-2-one;

1-[1-[1-(2-Bromobenzyl)piperidin-4-yl]piperidin-4-yl]-1,3-dihydro-2H-benzimidazol-2-one;

1-[1-[1-(2-Hydroxybenzyl)piperidin-4-yl]piperidin-4yl]-1,3-dihydro-2H-benzimidazol-2-one;

1-[1-[1-(2-Iodobenzyl)piperidin-4-yl]piperidin-4-yl]-1,3-dihydro-2H-benzimidazol-2-one; 1-[1-[1-[(3-Methyl-2-thienyl)methyl]piperidin-4-yl]piperidin-4-yl]-1,3dihydro-2H-benzimidazol-2-one;

1-[1-[1-[(5-Methyl-2-thienyl)methyl]piperidin-4-yl]piperidin-4-yl]-1,3-dihydro-2H-benzimidazol-2-one;

1-[1-[1-[(3-Bromo-2-thienyl)methyl]piperidin-4-yl]piperidin-4-yl]-1,3-dihydro-2H-benzimidazol-2-one;

1-[1-[1-[2-(Methoxycarbonyl)benzyl]piperidin-4-yl]piperidin-4-yl]-1,3-dihydro-2H-benzimidazol-2-one;

1-[1-[1-[(Thieno[2,3-b]thien-2-yl)methyl]piperidin-4-yl]piperidin-4-yl]-1,3-dihydro-2H-benzimidazol-2-one;

1-[1-[1-[(3-Chloro-2-thienyl)methyl]piperidin-4-yl]piperidin-4-yl]-1,3-dihydro-2H-benzimidazol-2-one;

1-[1-[1-(2-Ethylbenzyl)piperidin-4-yl]piperidin-4-yl]-1,3-dihydro-2H-benzimidazol-2 one;

1-[1-[1-(3-Methyl-2-furoyl)piperidin-4-yl]piperidin-4-yl]-1,3-dihydro-2H-benzimidazol-2-one;

1-[1-[1-(3-Methylfurfuryl)piperidin-4-yl]piperidin-4-yl]-1,3-dihydro-2H-benzimidazol-2-one;

1-[1-[1-(Thiazol-5-ylmethyl)piperidin-4-yl]piperidin-4-yl]-1,3-dihydro-2H-benzimidazol-2-one;

1-[1-[1-[(1-Methyl-1H-imidazol-4-yl)methyl]piperidin-4-yl]piperidin-4-yl]-1,3-dihydro-2H-benzimidazol-2-one;

1-[1-[1-[(5-Methyl-3-methylthio-isothiazol-4-yl)methyl]piperidin-4-yl]piperidin-4-yl]-1,3-dihydro-2H-benzimidazol-2-one;

1-[1-[1-[(4-Methyl-1,2,3-thiadiazol-5-yl)methyl]piperidin-4-yl]piperidin-4-yl]1,3-dihydro-2H-benzimidazol-2-one;

1-[1-[1-[(Isoxazol-5-yl)methyl]piperidin-4-yl]piperidin-4-yl]-1,3-dihydro-2H-benzimidazol-2-one;

1-[1-[1-[(Thiazol-2-yl)methyl]piperidin-4-yl]piperidin-4-yl]-1,3-dihydro-2H-benzimidazol-2-one;

1-[1-[1-(2-Mesylbenzyl)piperidin-4-yl]piperidin-4-yl]-1,3-dihydro-2H-benzimidazol-2-one;

5-Bromo-1-[1-[1-(2-methylbenzyl)piperidin-4-yl]piperidin-4-yl]-1,3-dihydro-2H-benzimidazol-2-one; or 5-Bromo-1-[1-[1-[(3-methyl-2-thienyl)methyl]piperidin-4-yl]piperidin-4-yl]--1,3-dihydro-2H-benzimidazol-2-one, or a pharmaceutically acceptable salt, enantiomer, diastereomer or mixture thereof.

The invention is described herein in detail using the terms defined below unless otherwise specified. The compounds of the present invention may have asymmetric centers, chiral axes and chiral planes, and occur as racemates, diastereomeric, mixtures, and as individual diastereomers, with all possible isomers, including optical isomers, being included in the present invention. (See E. L. Eliel and S. H. Wilen *Stereochemistry of Carbon Compounds* (John Wiley and Sons, New York 1994), in particular pages 1119-1190). There may exist tautomers, which are also included in the present invention.

When any variable (e.g. aryl, heterocycle, R, $R^a$ etc.) occurs more than one time in any constituent, its definition on each occurrence is independent at every other occurrence. Also, combinations of substituents/or variables are permissible only if such combinations result in stable compounds.

The term "alkyl" refers to a monovalent alkane (hydrocarbon) derived radical containing from 1 to 10 carbon atoms unless otherwise defined. It may be straight, or branched. Preferred alkyl groups include methyl, ethyl, propyl, isopropyl, butyl, t-butyl, cyclopropyl cyclopentyl and cyclohexyl. When the alkyl group is said to be substituted with an alkyl group, this is used interchangeably with "branched alkyl group".

"Alkyl optionally substituted with fluoro" refers to an alkyl group optionally substituted with 1, 2 or 3 atoms of fluorine. Examples of such group include trifluoromethyl, difluoromethyl and 2,2,2-trifluoroethyl, in addition to aforesaid examples of alkyl group.

Cycloalkyl is a species of alkyl containing from 3 to 15 carbon atoms, unless otherwise defined, without alternating or resonating double bonds between carbon atoms. It may contain from 1 to 4 rings, which are fused. Examples of such cycloalkyl elements include, but are not limited to, cyclopropyl, cyclobutyl, cyclopentyl, cyclohexyl and cycloheptyl.

Alkoxy refers to an alkyl group of indicated number of carbon atoms attached through an oxygen bridge, with the alkyl group optionally substituted as described herein. Said groups are those groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentyloxy, isopentyloxy, hexyloxy, isohexyloxy allyloxy, propargyloxy, and the like.

The term "alkenyl" refers to a monovalent alkene-derived radical containing from 2 to 6 carbon atoms unless otherwise defined. Preferred alkenyl group include vinyl, allyl and 1-propenyl.

The term "alkynyl" refers to a monovalent alkyne-derived radical containing from 2 to 6 carbon atoms unless otherwise defined. Preferred alkynyl groups include ethynyl, 1-propynyl and 2-propynyl.

Halogen (halo) refers to chlorine, fluorine, iodine or bromine.

Aryl refers to aromatic rings e.g., phenyl, substituted phenyl and the like, as well as rings which are fused, e.g., naphthyl, phenanthrenyl and the like, or those which are assembled, e.g., biphenylyl. An aryl group thus contains at least one ring having at least 6 atoms, with up to five such rings being present, containing up to 22 atoms therein unless otherwise defined, with alternating (resonating) double bonds between adjacent carbon atoms. Examples of aryl groups are phenyl, naphthyl, tetrahydronaphthyl, indanyl, biphenylyl, azulenyl, anthryl or acenaphthyl and phenanthrenyl, preferably phenyl, naphthyl or phenanthrenyl. Aryl groups may likewise be substituted as defined. Preferred substituted aryls include phenyl and naphthyl.

The term heterocyclyl or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. A fused heterocyclic ring system may include carbocyclic rings and need include only one heterocyclic ring. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl. An embodiment of the examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, 2-pyridinonyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

The term "heteroatom" means O, S or N, selected on an independent basis.

The term "heteroaryl" refers to a monocyclic aromatic hydrocarbon group having 5 or 6 ring atoms, or a bicyclic aromatic group having 8 to 12 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of such heterocyclic elements include, but are not limited to, acridinyl, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, isoxazolyl, oxadiazolyl, oxazolyl, pyridyl, pyrazinyl, pyrazolyl, pyridazinyl, pyrimidinyl, pyrrolyl, quinazolinyl, quinolyl, quinoxalinyl, tetrahydroisoquinolyl, tetrahydroquinolyl, tetrazolyl, thiadiazolyl, thiazolyl, thienofuryl, thienothienyl, thienyl and triazolyl.

This invention is also concerned with a method of treating ocular hypertension or glaucoma by administering to a patient in need thereof one of the compounds of formula I in combination with a β-adrenergic blocking agent such as timolol, carbonic anhydrase inhibitor such as dorzolamide, acetazolamide, methazolamide or brinzolamide, potassium channel blocker, a prostaglandin such as latanoprost, isopropyl unoprostone, S1033 or a prostaglandin derivative such as a hypotensive lipid derived from PGF2α prostaglandins. An example of a hypotensive lipid (the carboxylic acid group on the α-chain link of the basic prostaglandin structure is replaced with electrochemically neutral substituents) is that in which the carboxylic acid group is replaced with CH2—OR group such as $CH_2OCH_3$ ($PGF_{2\alpha}$ 1-$OCH_3$), or a $CH_2OH$ group ($PGF_{2\alpha}$ 1-OH). Preferred potassium channel blockers for use in combination with the M1 agonist are calcium activated potassium channel blockers. More preferred potassium channel blockers are high conductance, calcium activated potassium (Maxi-K) channel blockers.

Macular edema is swelling within the retina within the critically important central visual zone at the posterior pole of the eye. An accumulation of fluid within the retina tends to detach the neural elements from one another and from their local blood supply, creating a dormancy of visual function in the area.

Glaucoma is characterized by progressive atrophy of the optic nerve and is frequently associated with elevated intraocular pressure (IOP). It is possible to treat glaucoma, however, without necessarily affecting IOP by using drugs that impart a neuroprotective effect. See Arch. Ophthalmol. Vol. 112, January 1994, pp. 37-44; Investigative Ophthalmol. & Visual Science, 32, 5, April 1991, pp. 1593-99. It is believed that M1 agonist which lower IOP are useful for providing a neuroprotective effect. They are also believed to be effective for treating macular edema and/or macular degeneration, increasing retinal and optic nerve head blood velocity and increasing retinal and optic nerve oxygen by lowering IOP, which when coupled together benefits optic nerve health. As a result, this invention further relates to a method for treating macular edema and/or macular degeneration, increasing retinal and optic nerve head blood velocity, increasing retinal and optic nerve oxygen tension as well as providing a neuroprotective effect or a combination thereof.

Depression is related to a decrease in neurotransmitter release. Current treatments of depression include blockers of neurotransmitter uptake, and inhibitors of enzymes involved in neurotransmitter degradation which act to prolong the lifetime of neurotransmitters.

Alzheimer's disease is also characterized by a diminished neurotransmitter release. Alzheimer's disease is a neurodegenerative disease of the brain leading to severely impaired cognition and functionality. This disease leads to progressive regression of memory and learned functions. Alzheimer's disease is a complex disease that affects cholinergic neurons, as well as serotonergic, noradrenergic and other central neurotransmitter systems. Manifestations of Alzheimer's disease extend beyond memory loss and include personality changes, neuromuscular changes, seizures, and occasionally psychotic features.

Alzheimer's disease is the most common type of dementia in the United States. Some estimates suggest that up to 47% of those older than 85 years have Alzheimer's disease. Since the average age of the population is on the increase, the frequency of Alzheimer's disease is increasing and requires urgent attention. Alzheimer's is a difficult medical problem because there are presently no adequate methods available for its prevention or treatment.

Three classes of drugs are being investigated for the treatment of Alzheimer's disease. The first class consists of compounds that augment acetylcholine neurotransmitter function. Currently, cholinergic potentiators such as the anticholinesterase drugs are being used in the treatment of Alzheimer's disease. In particular, physostigmine (eserine), an inhibitor of acetylcholinesterase, has been used in its treatment. The administration of physostigmine has the drawback of being considerably limited by its short half-life of effect, poor oral bioavailability, and severe dose-limiting side-effects, particularly towards the digestive system. Tacrine (tetrahydroaminoacridine) is another cholinesterase inhibitor that has been employed; however, this compound may cause hepatotoxicity.

A second class of drugs that are being investigated for the treatment of Alzheimer's disease is nootropics that affect neuron metabolism with little effect elsewhere. These drugs improve nerve cell function by increasing neuron metabolic activity. Piracetam is a nootropic that may be useful in combination with acetylcholine precursors and may benefit Alzheimer's patients who retain some quantity of functional acetylcholine release in neurons. Oxiracetam is another related drug that has been investigated for Alzheimer treatment.

A third class of drugs is those drugs that affect brain vasculature. A mixture of ergoloid mesylates is used for the treatment of dementia. Ergoloid mesylates decrease vascular resistance and thereby increase cerebral blood flow. Also employed are calcium channel blocking drugs including nimodipine which is a selective calcium channel blocker that affects primarily brain vasculature.

Other miscellaneous drugs are targeted to modify other defects found in Alzheimer's disease. Selegiline, a monoamine oxidase B inhibitor which increases brain dopamine and norepinephrine has reportedly caused mild improvement in some Alzheimer's patients. Aluminum chelating agents have been of interest to those who believe Alzheimer's disease is due to aluminum toxicity. Drugs that affect behavior, including neuroleptics, and anxiolytics have been employed. Side effects of neuroleptics range from drowsiness and anti cholinergic effects to extrapyramidal side effects; other side effects of these drugs include seizures, inappropriate secretion of antidiuretic hormone, jaundice, weight gain and increased confusion. Anxiolytics, which are mild tranquilizers, are less effective than neuroleptics, but also have milder side effects. Use of these behavior-affecting drugs, however, remains controversial. The present invention is related to novel compounds which are useful as M1 agonists. It is believed that certain diseases such as depression, memory disorders and Alzheimer's disease are the result of an impairment in neurotransmitter release. The M1 agonists of the present invention may therefore be utilized as cell excitants which should stimulate an unspecific release of neurotransmitters such as acetylcholine, serotonin and dopamine. The compounds of this invention are also useful for treating pain. Enhanced neurotransmitter release should reverse the symptoms associated with depression and Alzheimer's disease.

The compounds within the scope of the present invention exhibit M1 agonist activity and thus are useful in disorders associated with muscarinic receptor malfunction. A number of cognitive disorders such as Alzheimer's Disease, schizophrenia, memory loss or depression may benefit from enhanced release of neurotransmitters such as serotonin, dopamine or acetylcholine and the like. Stimulation of M1 receptors maintains cellular depolarization and therefore enhances secretion of these vital neurotransmitters.

The compounds of this invention may be combined with anticholinesterase drugs such as physostigmine (eserine), donepezil, and tacrine (tetrahydroaminoacridine), nootropics such as piracetam, oxiracetam, ergoloid mesylates, selective calcium channel blockers such as nimodipine, or monoamine oxidase B inhibitors such as selegiline, in the treatment of Alzheimer's disease.

For use in medicine, the salts of the compounds of formula I will be pharmaceutically acceptable salts. Other salts may, however, be useful in the preparation of the compounds according to the invention or of their pharmaceutically acceptable salts. When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N,N$^1$-dibenzylethylenediamine, diethylamine, 2-diethylaminoethanol, 2dimethylaminoethanol, ethanolamine, ethylenediamine, N-ethylmorpholine, N-ethylpiperidine, glucamine, glucosamine, histidine, hydrabamine, isopropylamnine, lysine, methylglucamine, morpholine, piperazine, piperidine, polyamine resins, procaine, purines, theobromine, triethylamine, trimethylaamine tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, sex and response of the individual patient, as well as the severity of the patient's symptoms.

The M1 muscarinic agonist used can be administered in a therapeutically effective amount orally, intravenously, subcutaneously, topically, transdermally, parenterally or any other method known to those skilled in the art. Ophthalmic pharmaceutical compositions are preferably adapted for topical administration to the eye in the form of solutions, suspensions, ointments, creams or as a solid insert. Ophthalmic formulations of this compound may contain from 0.01 to 5% and especially 0.1 to 2% of medicament. Higher dosages as, for example, about 10% or lower dosages can be employed provided the dose is effective in reducing intraocular pressure, treating glaucoma, increasing blood flow velocity or oxygen tension. For a single dose, from between 0.001 to 5.0 mg, preferably 0.005 to 2.0 mg, and especially 0.005 to 1.0 mg of the compound can be applied to the human eye.

The pharmaceutical preparation that contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopalmitate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a microparticle formulation. The pharmaceutical preparation may also be in the form of a solid insert. For example, one may use a solid water soluble polymer as the carrier for the medicament. The polymer used to form the insert may be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts, ethylacrylates, polyactylamides; natural products such as gelatin, alginates, pectins, tragacanth, karaya, chondrus, agar, acacia; the starch derivatives such as starch acetate, hydroxymethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, gellan gum, and mixtures of said polymer.

Suitable subjects for the administration of the formulation of the present invention include primates, man and other animals, particularly man and domesticated animals such as cats and dogs.

The pharmaceutical preparation may contain non-toxic auxiliary substances such as antibacterial components which are non-injurious in use, for example, thimerosal, benzalkonium chloride, methyl and propyl paraben, benzyldodecinium bromide, benzyl alcohol, chlorhexidine, or phenylethanol; buffering ingredients such as sodium borate, sodium acetate, sodium citrate, or gluconate buffers; and other conventional ingredients such as sodium chloride, sorbitan monolaurate, triethanolamine, polyoxyethylene sorbitan monopalmitate, ethylenediaminetetraacetic acid, and the like.

The ophthalmic solution or suspension may be administered as often as necessary to maintain an acceptable IOP level in the eye. It is contemplated that administration to the mammalian eye will be once to three times daily.

For topical ocular administration the novel formulations of this invention may take the form of solutions, gels, ointments, suspensions or solid inserts, formulated so that a unit dosage comprises a therapeutically effective amount of the active component or some multiple thereof in the case of a combination therapy.

The following examples given by way of illustration is demonstrative of the present invention and are non-limiting of the invention.

Method 1

The compounds of formula I (Z=CO) can be prepared from the intermediate A and arylcarboxylic acid.

Formula 1

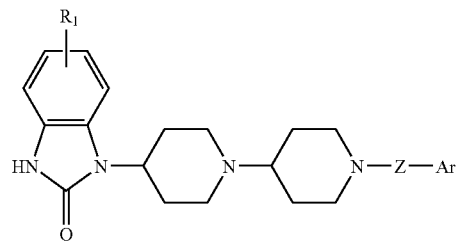

-continued

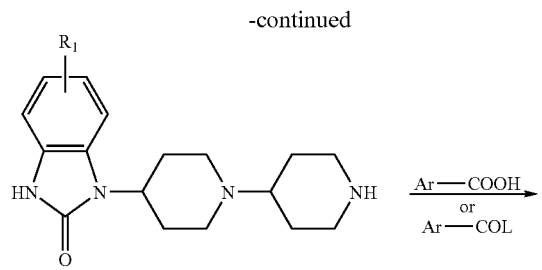

Intermediate A

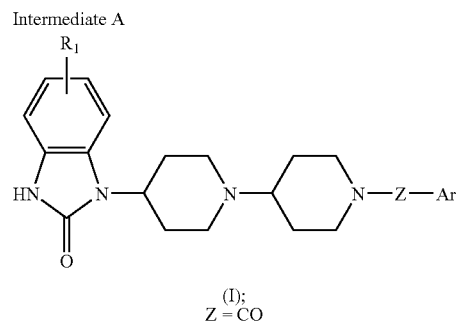

(I); Z = CO

The reaction can be performed in the presence of a condensing agent such as, for example, di(cyclohexyl)carbodiimide, ethyl 3-(dimethylamino)propyl carbodiimide in an inert solvent such as chloroform, dichloromethane, N,N-dimethylformamide, or a mixture thereof.

In this reaction, carboxylic acid derivatives Ar—COL (L is an appropriate leaving group such as chloro, bromo, 1,2,3-benzotriazolyl-1-oxy and alkyloxycarbonyloxy) can be used in place of the corresponding carboxylic acid. The examples of said derivatives are acyl halides such as acyl chloride and acyl bromide, esters such as methyl ester, phenyl ester, and 1,2,3-benzotriazolyl-1-oxy ester, thioesters such as thiocarboxylic acid S-methyl ester, and mixed anhydrides such as acyl ethoxycarbonyl anhydride and acyl isobutyloxycarbonyl anhydride.

In this and the following preparative methods, the reaction products may be isolated from the reaction mixture according to generally known procedures such as extraction, chromatography, sublimation, and crystallization.

The amide derivative obtained (i.e. Formula I; Z=CO) may be converted into corresponding amine (i.e. Formula I; Z=CH$_2$) using a reducing agent such as lithium aluminum hydride. This reaction can be performed in an inert solvent such as lithium aluminum hydride. This reaction can be performed in an inert solvent such as tetrahydrofuran, diethyl ether, diisopropyl ether, 1,2-dimethoxyethane, or 1,4-dioxane.

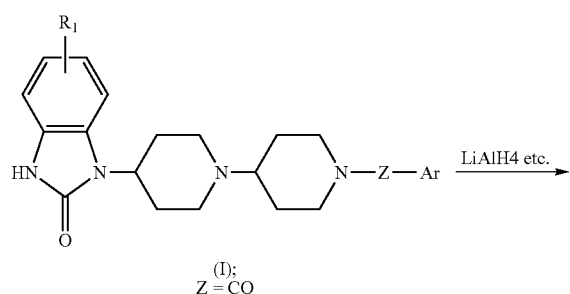

(I); Z = CO

-continued

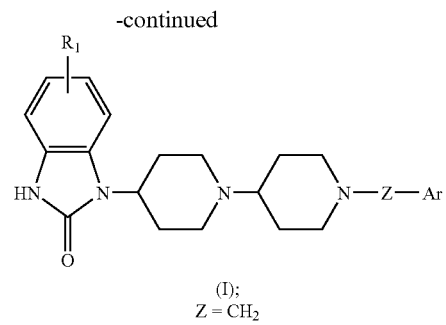

(I); Z = CH$_2$

Method 2

The compounds of formula I can also be prepared as follows:

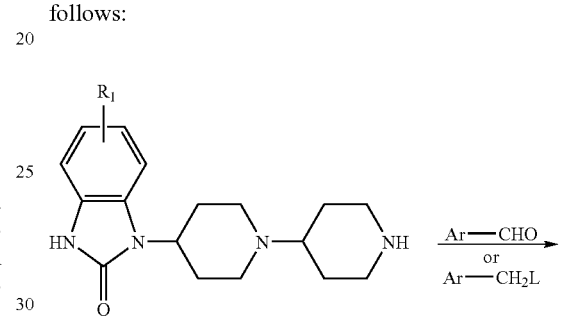

Intermediate A

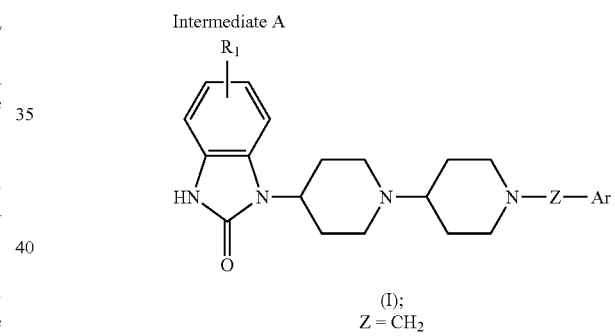

(I); Z = CH$_2$

The intermediate A can be prepared as described in WO96/13262 and WO01/27104. The N-alkylation may be performed reductively with an aldehyde Ar—CHO, or may be performed with Ar—CH2-L (L represents an appropriate leaving group such as chloro, bromo, iodo, tosyloxy, and mesyloxy).

Said reductive N-alkylation may be performed in the presence of a reducing agent such as sodium borohydride, zinc borohydride, sodium cyanoborohydride, or sodium triacetoxyborohydride, in an inert solvent such as dimethylformamide, chloroform, dichloromethane, ethanol, isopropyl alcohol, toluene, or a mixture thereof. A catalyst such as acetic acid, zinc halide or titanium alkoxide may be added to the reaction mixture.

Said reductive alkylation may also be performed under hydrogen atmosphere in the presence of a catalyst such as palladium/carbon, palladium/CaSO4 or platinum/carbon. Adding a dehydrating agent such as magnesium sulfate, p-toluenesulfonic acid, or aluminum tert-butoxide, or using a water separator such as Dean-Stark apparatus may be useful for accelerating the reaction. The dehydration process may be performed simultaneously with or precedently to the reduction process.

When ArCH$_2$-L is reacted with the intermediate A, a base such as sodium carbonate, potassium carbonate, cesium carbonate, sodium hydrogen carbonate, triethylamine, ethyldiisopropylamine and pyridine can be utilized for accelerating the reaction. Usually the reaction is performed in an reaction-inert solvent such as dimethylformamide, dimethyl sulfoxide or chloroform.

Method 3

The compounds of formula I may also be prepared by N-alkylating the intermediate B that is commercially available or alternatively made as described in, for example, WO 96/13262 and JP 10330377.

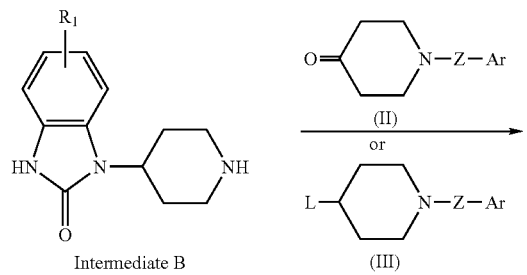

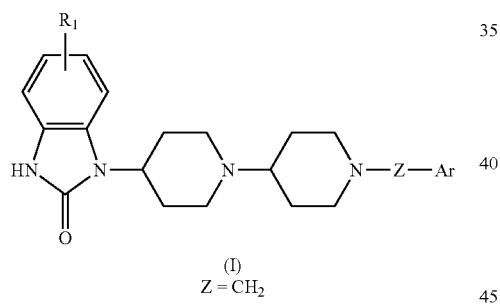

The intermediate B may be reductively alkylated with a compound of formula II, or alkylated with a compound of formula III (L represents an appropriate leaving group such as tosyloxy, mesyloxy, iodo, bromo).

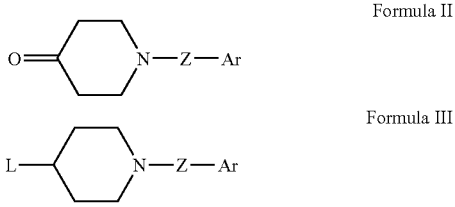

These reactions can be performed in conditions described in method 2.

The following examples given by way of illustration is demonstrative of the present invention.

EXAMPLE 1

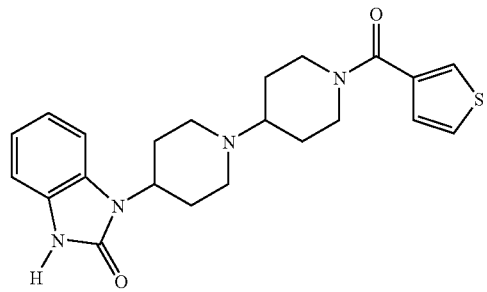

1-[1-[1-(3-Thenoyl)piperidin-4-yl]piperidin-4-yl]-1,3-dihydro-2H-benzimidazol-2one A mixture of 72 mg of 3-thenoic acid, 187 mg of 1-[1-(piperidin-4-yl)piperidin-4-yl]-1,3-dihydro-2H-benzimidazol-2-one dihydrochloride, 110 mg of ethyl 3-(dimethylamino)propylcarbodiimide, 110 mg of 1-hydroxy-1,2,3-benzotriazole, 300 mg of triethylamine, 10 ml of CHCl3, and 10 ml of tert-butyl alcohol was stirred for 17 h. The reaction mixture was partitionized between chloroform and aqueous NaHCO$_3$. The organic layer was washed with aqueous NaHCO$_3$, dried over anhydrous Na$_2$SO$_4$, and concentrated. The residue was purified on SiO$_2$ chromatography (chloroform/methanol=30:1-20:1) to afford 180 mg of 1-[1-[1-(3-thenoyl)piperidin-4-yl]piperidin-4-yl]-1,3-dihydro-2H-benzimidazol-2-one as a colorless amorphous.

$^1$H-NMR(300 MHz, CDCl$_3$) 1.45-1.70(2H, m), 1.8-2.0 (4H, m), 2.35-2.55(4H, m), 2.58-2.72(1H, m), 2.7-3.2(4H, m), 4.0-4.8(3H, m)7.00-7.22(4H, m),7.26-7.55(3H, m), 9.45 (1H, brs)

MS [M+H]$^+$=411

EXAMPLE 2

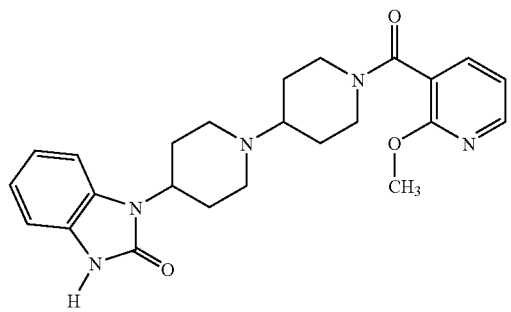

1-[1-[1-(2-Methoxynicotinoyl)piperidin-4-yl]piperidin-4-yl]-1,3-dihydro-2H-benzimididazol-2one From 2-Methoxynicotinoic acid using the same procedure as described for example 1, there was obtained a colorless amorphous.

$^1$H-NMR(300 MHz, CDCl$_3$) 1.40-2.00(6H, m), 2.30-3.20 (9H, m), 3.44-3.59(1H,m), 3.98(3H, s), 4.25-4.40(1H, m), 4.75-4.90(1H, m), 6.90-7.12(4H, m), 7.18-7.35(1H, m), 7.48-7.62(1H, m), 8.20(1H, dd, J=2.9Hz, J=5.0Hz), 8.93 (1H, brs)

MS [M+H]$^+$=436

The following examples 3-16 were made in the same manner as described in detail above using commercially available starting materials.

EXAMPLE 3

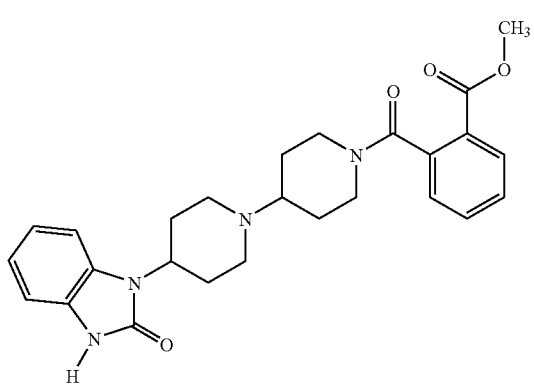

1-[1-[1-[2-(Methoxycarbonyl)benzoyl]piperidin-4-yl]piperidin-4-yl]-1,3-dihydro-2H-benzimidazol-2-one $^1$H-NMR(300 MHz, CDCl$_3$) 1.40-1.93(4H, m), 2.00(1H, brd, J=10.8Hz), 2.28(1H, brs), 2.35-2.56(4H, m), 2.56-2.72 (1H, m), 2.83(1H, brt, J=12.3Hz), 2.91-3.18(3H,m), 3.44 (1H, brd, J=12.6Hz), 3.89(3H, s), 4.24-4.46(1H, m), 4.86 (1H, brd, J=12.6Hz), 7.00-7.14(3H, m), 7.24-7.34(2H, m), 7.45(1H, dt, J=1.4Hz, 7.7Hz), 7.57(1H, dt, J=1.4Hz, 7.7Hz), 8.03(1H, dd, J=1.4Hz, 7.7Hz).

MS [M+H]$^+$=463

Colorless oil.

EXAMPLE 4

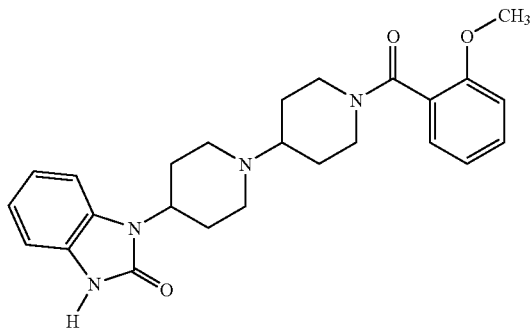

1-[1-[1-(2-Methoxybenzoyl)piperidin-4-yl]piperidin-4-yl]-1,3-dihydro-2H-benzimidazol-2one 1H-NMR(300 MHz, CDCl$_3$) 1.4-2.05(6H,m), 2.30-3.20 (9H,m), 3.55-3.65(1H,m), 3.83&3.85(3H,2s), 4.25-4.40(1H, m), 4.80-4.95(1H,m), 6.87-7.10(5H,m), 7.19-7.39(3H,m), 8.88(1H,brs)

MS [M+H]$^+$=435

Colorless amorphous.

EXAMPLE 5

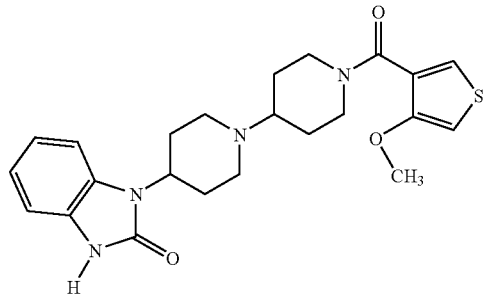

1-[1-[1-(4-Methoxy-3-thenoyl)piperidin-4-yl]piperidin-4-yl]-1,3-dihydro-2H-benzimidazol-2-one $^1$H-NMR(300 MHz, CDCl$_3$) 1.45-1.64(2H, m), 1.72-2.13 (4H, m), 2.38-2.62(4H, m), 2.63-2.90(2H, m), 3.00-3.25(4H, m), 3.65-3.80(1H, m), 3.85(3H, s), 4.22-4.40(1H, m), 6.55 (1H, d, J=3.3Hz), 7.00-7.12(3H, m), 7.35-7.45(1H, m), 7.47(1H, d, J=3.3Hz), 7.89(1H, brs)

MS [M+H]$^+$=441

Colorless powder.

EXAMPLE 6

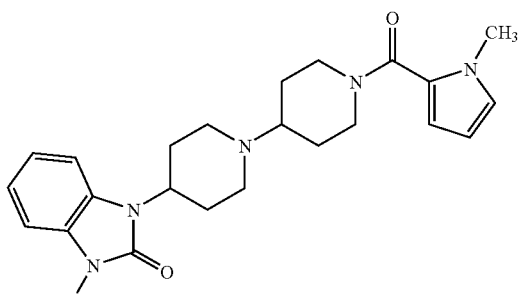

1-[1-[1-[(1-Methyl-2-pyrrolyl)carbonyl]piperidin-4-yl]piperidin-4-yl]-1,3-dihydro-2H-benzimidazol-2one $^1$H-NMR(300 MHz, CDCl$_3$) 1.48-4.45(19H, m), 4.52-4.68(2H, m), 6.05-6.12(1H, m), 6.30-6.38(1H, m), 6.67-6.72 (1H, m), 7.00-7.12(3H, m), 7.18-7.36(1H, m), 8.70-9.02(1H, m)

MS [M+H]$^+$=408,

Colorless amorphous.

EXAMPLE 7

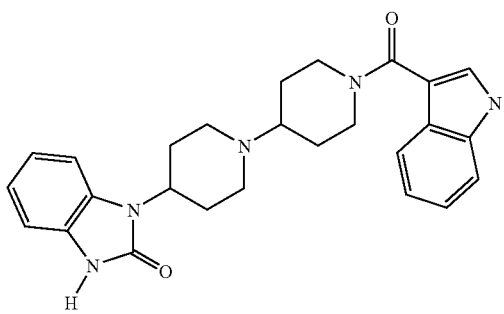

1-[1-[1-[(3-Indolyl)carbonyl]piperidin-4-yl]piperidin-4-yl]-1,3-dihydro-2H-benzimidazol-2-one $^1$H-NMR(300 MHz, CDCl$_3$)
MS [M+H]$^+$=444
Colorless powder.

EXAMPLE 8

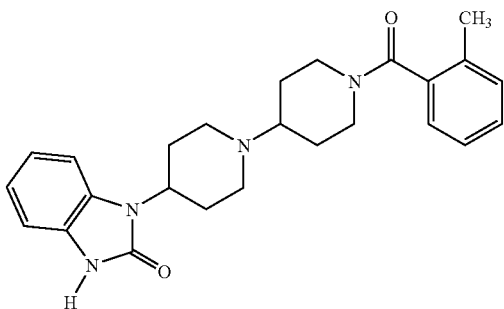

1-[1-[1-(2-Methylbenzoyl)piperidin-4-yl]piperidin-4-yl]-1,3-dihydro-2H-benzimidazol-2-one $^1$H-NMR(300 MHz, CDCl$_3$) 1.17-2.08(8H, m), 2.08-2.70 (7H, m), 2.70-2.89(1H, m), 2.89-3.18(2H, m), 3.48-3.62(1H, m), 4.26-4.44(1H, m), 4.80-4.95(1H, m), 6.97-7.35(8H, m), 8.35-8.62(1H, m)
MS [M+H]$^+$=419
Colorless solid.

EXAMPLE 9

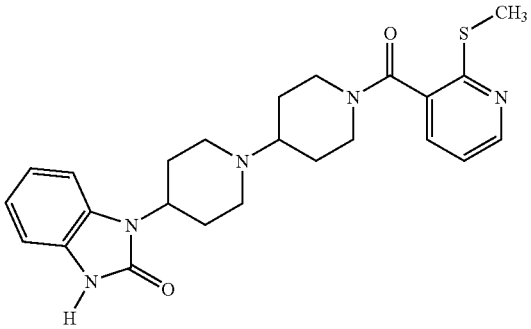

1-[1-[1-[2-(Methylthio)nicotinoyl]piperidin-4-yl]piperidin-4-yl]-1,3-dihydro-2H-benzimidazol-2-one $^1$H-NMR(300 MHZ, CDCl$_3$) 1.50-2.10(6H, m), 2.30-2.70 (5H, m), 2.59(3H, s), 2.75-2.92(1H, m), 2.95-3.20(3H, m), 3.40-3.60(1H, m), 4.25-4.45(1H, m), 4.75-4.90(1H, m), 6.98-7.15(4H, m), 7.20-7.32(1H, m), 7.42(1H, d, J=7.2Hz), 8.48(1H, d, J=4.8Hz), 9.56(1H, s)
MS [M+H]$^+$=419

Pale yellow amorphous.

EXAMPLE 10

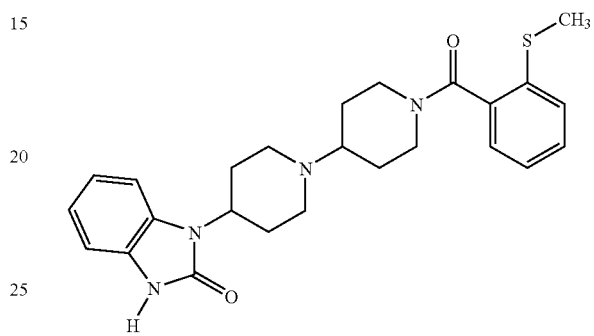

1-[1-[1-[2-(Methylthio)benzoyl]piperidin-4yl]piperidin-4-yl]-1,3-dihydro-2H-benzimidazol-2-one $^1$H-NMR(300 MHz, CDCl$_3$) 1.55-2.20(8H, m), 2.33-3.20 (1H, m), 4.28-4.42(1H, m), 4.80-4.97(1H, m), 7.00-7.49(8H, m)
MS [M+H]$^+$=451

Pale yellow oil.

EXAMPLE 11

EXAMPLE 12

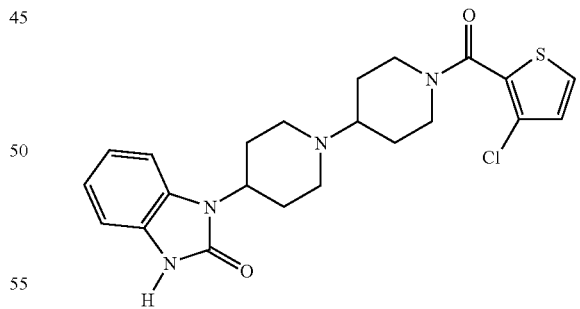

1-[1-[1-(3-Chloro-2-thenoyl)piperidin-4-yl]piperidin-4-yl]-1,3-dihydro-2H-benzimidazol-2-one $^1$H-NMR(300 MHz, CDCl$_3$) 1.35-4.90(18H, m), 6.88-6.93(1H, m), 6.98-7.14(3H,m) 7.18-7.33(1H, m), 7.34-7.39 (1H, m), 9.20-9.38(1H, m)
MS [M+H]$^+$=445

Colorless solid.

EXAMPLE 13

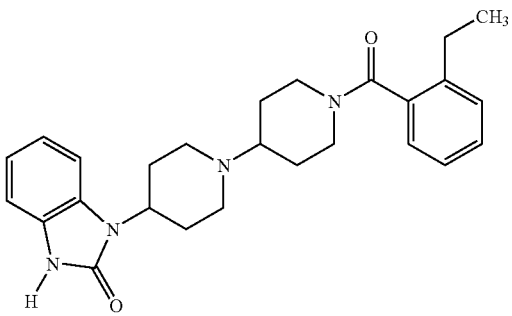

1-[1-[1-(2-Ethylbenzoyl)piperidin-4-yl]piperidin-4-yl]-1,3-dihydro-2H-benzimidazol-2-one $^1$H-NMR(300 MHz, CDCl$_3$) 1.21&1.27(3H, t, J=7.5Hz), 1.35-3.13(17H, m), 3.49-3.63(1H, m), 4.25-4.41(1H, m), 4.82-4.93(1H, m), 7.01-7.36(8H, m), 8.15(1H, brs)
MS [M+H]$^+$=433
Colorless powder.

EXAMPLE 14

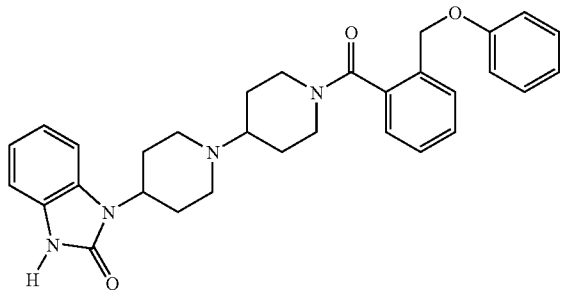

1-[1-[1-[2-(Phenoxymethyl)benzoyl]piperidin-4-yl]piperidin-4-yl]-1,3-dihydro-2H-benzimidazol-2-one $^1$H-NMR(300 MHz, CDCl$_3$) 1.20-3.18(15H, m), 3.50-3.80(1H, m), 4.10-4.40(1H, m), 4.70-5.28(3H, m), 6.88-7.59 (13H, m), 8.96(1H, brs)
MS [M+H]+=511
Colorless amorphous.

EXAMPLE 15

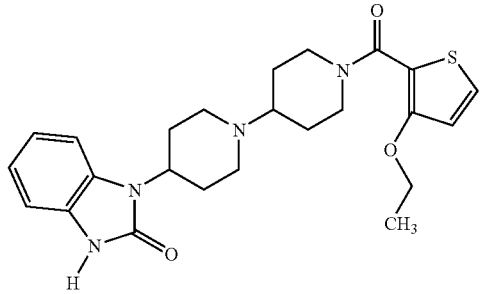

1-[1-[1-(3-Ethoxy-2-thenoyl)piperidin-4-yl]piperidin-4-yl]-1,3-dihydro-2H-benzimidazol-2-one $^1$H-NMR(300 MHz, CDCl$_3$) 1.35-1.43(3H, m), 1.53-4.48 (18H, m), 408-4.18(2H, m), 6.73-6.77(1H, m), 7.02-7.12 (3H, m), 7.25-7.38(2H, m), 9.07-9.15(1H, m)
MS [M+H]$^+$=455

Colorless amorphous.

EXAMPLE 16

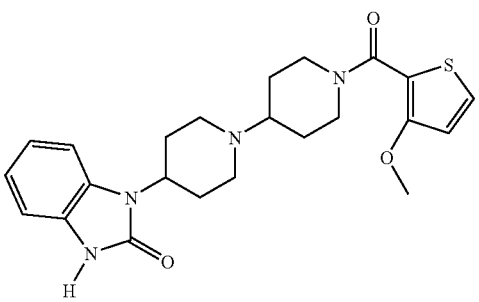

1-[1-[1-(3-Methoxy-2-thenoyl)piperidin-4-yl]piperidin-4-yl]-1,3-dihydro-2H-benzimidazol-2-one $^1$H-NMR(300 MHz, CDCl$_3$) 1.50-4.05(19H, m), 4.22-4.45(2H, m), 6.79(1H, d, J=5.4Hz), 7.00-7.14(3H, m), 7.24-7.36(1H, m), 7.33(1H, d, J=5.4Hz), 9.06(1H, brs)
MS [M+H]$^+$=441 slightly yellowish foam

EXAMPLE 17

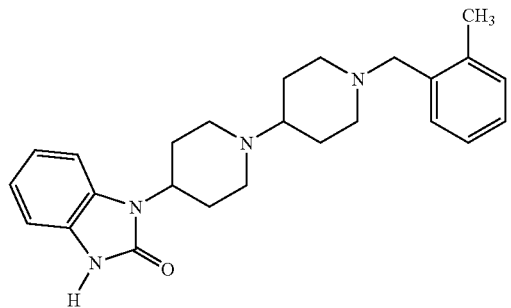

1-[1-[1-(2-Methylbenzyl)piperidin-4-yl]piperidin-4yl]-1,3-dihydro-2H-benzimidazol-2-one Step 1. Synthesis of N-(2-Methylbenzyl)-4-piperidone To a suspension of 2.00 g of 4-piperidone monohydrate hydrochloride and 5.40 g of potassium carbonate in 30 ml of CH$_3$CN was added dropwise 1.57 ml of 2-methyl benzyl bromide at 0° C. After stirred at 0° C. or 3.5 h, the mixture was stirred at room temperature for an hour. At 0° C., the mixture was quenched with water and extracted with CHCl$_3$. The organic layer was washed with water, aqueous NaOH, and brine, and dried over anhydrous Na$_2$SO$_4$. The organic solvent was evaporated to give the crude product of 2.52 g of N-(2-methylbenzyl)-4-piperidone as a yellow oil.

Step 2. Synthesis of 1-[1-[1-(2-Methylbenzyl)piperidin-4-yl]piperidin-4-yl]-1,3-dihydro-2H-benzimidazol-2-one To a solution of 1.73 g of 4-(2-keto-1-benzimidazolyl)piperidine and 1.54 g of N-(2-methylbenzyl)4-piperidone in 20 ml of MeOH was added 51 ml of 0.3M methanolic solution of ZnCl$_2$—NaBH$_3$CN at room temperature. The reaction mixture was stirred at room temperature for 4 h and quenched with saturated aqueous NaHCO$_3$. The mixture was extracted with EtOAc, and the organic layer was washed with the 1:1 solution of saturated aqueous NaHCO$_3$ and brine, and dried over anhydrous Na$_2$SO$_4$. The organic solvent was evaporated and recrystallization of the residue from EtOAc gave 1.78 g of the target compound as a colorless powder.

$^1$H-NMR(300 MHz, CDCl$_3$) 1.50-1.70(2H, m), 1.72-1.90 (4H, m), 1.92-2.06(2H, m), 2.30-2.51(5H, m), 2.36(3H, s), 2.90-3.00(2H, m), 3.02-3.15(2H, m), 3.44(2H, s), 4.28-4.42 (1H, m), 7.00-7.10(3H, m), 7.11-7.08(3H, m), 7.23-7.37(2H, m), 8.74(1H, brs)

MS [M+H]$^+$=405

Colorless powder.

EXAMPLE 18

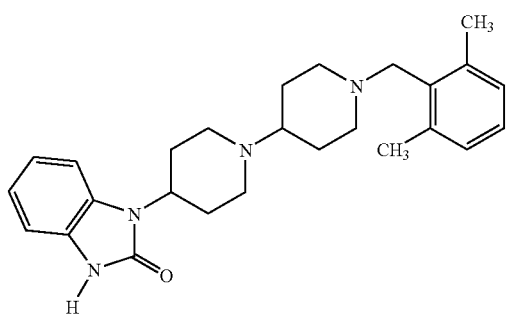

1-[1-[1-(2,6-Dimethylbenzyl)piperidin-4-yl]piperidin-4-yl]-1,3-dihydro-2H-benzimidazol-2-one To a solution of 19.8 mg of 1-[1-(piperidin-4-yl)piperidin-4-yl]-1,3-dihydro-2H-benzimidazol-2-one and 7.5 microliter of 2,6-dimethylbenzaldehyde in 1 ml of MeOH was added 274 microliter of 0.3M MeOH solution of ZnCl$_2$—NaBH$_3$CN at room temperature. The reaction mixture was stirred at room temperature for 2 h and quenched with saturated aqueous NaHCO$_3$. The mixture was extracted with EtOAc, and the organic layer was washed with the 1:1 solution of saturated aqueous NaHCO$_3$ and brine, and dried over anhydrous Na$_2$SO$_4$. The organic solvent was evaporated and the residue was purified with PNLC (CHCl$_3$/MeOH/28% aqueous NH$_3$=100/10/1) gave 11.8 mg of the target compound as a colorless solid.

$^1$H-NMR(300 MHz, CDCl$_3$) 1.42-1.60(2H, m), 1.71-1.88 (4H, m), 2.00-2.12(2H, m), 2.29-2.50(5H, m), 2.39(3H, s), 2.44(3H, s), 2.83-2.95(2H, m), 3.03-3.15(2H, m), 3.44(2H, s), 4.28-4.40(1H, m), 6.97-7.13(6l, m), 7.25-7.34(1H, m), 7.40-8.68(1H, m)

MS [M+H]$^+$=419 colorless powder

The following examples 19-30 were made in the same manner as described in detail above using an appropriate (hetero)arylcarboxaldehyde.

EXAMPLE 19

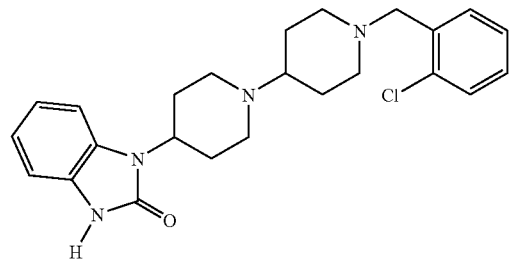

1-[1-[1-(2-Chlorobenzyl)piperidin-4-yl]piperidin-4-yl]-1,3-dihydro-2H-benzimidazol-2-one $^1$H-NMR(300 MHz, CDCl$_3$) 1.58-1.95(6H,m), 2.07-2.20 (2H,m), 2.35-2.55(5H,m),2.96-3.20(4H,m), 3.62(2H,s), 4.30-4.42(1H,m), 7.00-7.12(3H,m), 7.14-7.28(2H,m),7.29-7.38(2H,m),7.44-7.51 (1H,m),8.95-9.20(1H,m)

MS [M+H]$^+$=425 colorless foam

EXAMPLE 20

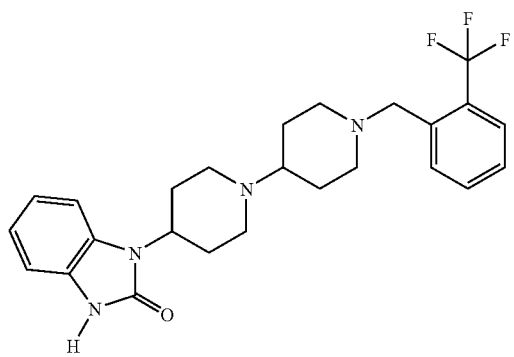

1-[1-[1-[2-(Trifluoromethyl)benzyl]piperidin-4-yl]piperidin-4-yl]-1,3-dihydro-2H-benzimidazol-2-one $^1$H-NMR(300 MHz, CDCl$_3$) 1.55-1.95(6H, m), 2.30-2.55 (5H, m), 2.02-2.18(2H, m), 2.88-3.02(2H, m), 3.03-3.20(2H, m), 3.65(2H, s), 4.28-4.43(1H, m), 7.0-7.13(3H, m), 7.26-7.40(2H, m), 7.52(1H, t, J=7.6Hz), 7.62(1H, d, J=7.9Hz), 7.81(1H, d, J=7.9Hz), 8.96(1H, brs)

MS [M+H]$^+$=459 colorless solid

EXAMPLE 21

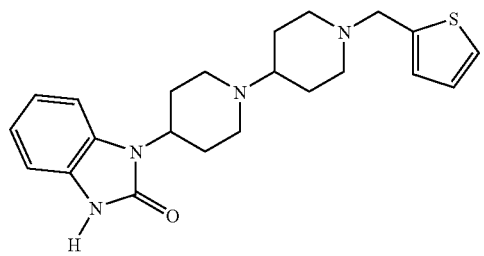

1-[1-[1-(2-Thienylmethyl)piperidin-4-yl]piperidin-4-yl]-1,3-dihydro-2H-benzimidazol-2-one ¹H-NMR(300 MHz, CDCl₃) 1.52-1.92(6H, m), 1.97-2.10 (2H, m), 2.30-2.52(5H, m), 2.98-3.16(4H, m), 3.73(2H, s), 4.23-4.40(1H, m), 6.87-6.97(2H, m), 6.98-7.10(3H, m), 7.20-7.25(1H, m), 7.27-7.35(1H, m), 8.50-9.20(1H, m)

MS [M+H]⁺=397 colorless solid

EXAMPLE 22

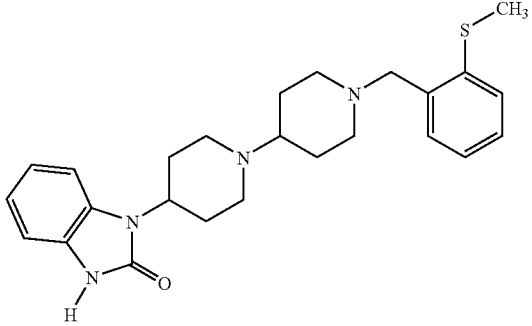

1-[1-[1-[2-(Methylthio)benzyl]piperidin-4-yl]piperidin-4-yl]-1,3-dihydro-2H-benzimidazol-2-one ¹H-NMR(300 MHz, CDCl₃) 1.53-1.90(6H, m), 2.00-2.12 (2H, m), 2.32-2.52(5H, m), 2.46(3H, s), 2.94-3.15(4H, m), 3.54(2H, s), 4.28-4.40(1H, m), 7.00-7.18(4H, m), 7.20-7.29 (2H, m), 7.30-7.38(2H, m), 8.88-9.15(1H, m)

MS [M+H]⁺=437 colorless foam

EXAMPLE 23

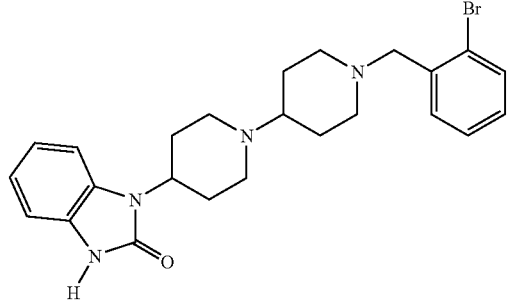

1-[1-[1-(2-Bromobenzyl)piperidin-4yl]piperidin-4-yl]-1,3-dihydro-2H-benzimidazol-2-one ¹H-NMR(300 MHz, CDCl₃) 1.55-1.92(6H, m), 2.07-2.20 (2H, m), 2.32-2.52(5H, m), 2.93-3.15(4H, m), 3.59(2H, s), 4.27-4.42(1H, m), 7.00-7.15(4H, m), 7.22-7.38(2H, m), 7.43-7.56(2H, m), 8.73(1H, brs)

MS [M+H]⁺=469, 471 colorless powder

EXAMPLE 24

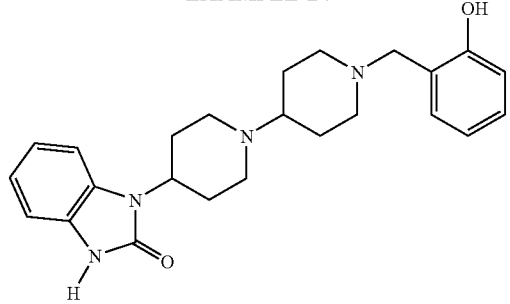

1-[1-[1-(2-Hydroxybenzyl)piperidin-4-yl]piperidin-4-yl]-1,3-dihydro-2H-benzimidazol-2-one ¹H-NMR(300 MHz, CDCl₃) 1.58-1.76(3H, m), 1.77-1.96 (4H, m), 2.06-2.20(2H, m), 2.30-2.52(5H, m), 3.00-3.18(4H, m), 3.70(2H, s), 4.28-4.41(1H, m), 6.74-6.87(2H, m), 6.94-7.00(1H, m), 7.01-7.12(3H, m), 7.13-7.21(1H, m), 7.23-7.36 (1H, m), 8.75-9.15(1H, m)

MS [M+H]⁺=407 pale pink powder

EXAMPLE 25

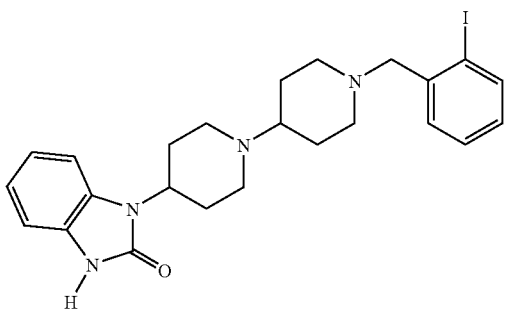

1-[1-[1-(2-Iodobenzyl)piperidin-4-yl]piperidin-4-yl-1,3-dihydro-2H-benzimidazol-2-one ¹H-NMR(300 MHz, CDCl₃) 1.52-1.72(2H m), 1.26-1.90 (4H, m), 2.07-2.18(2H, m), 2.32-2.52(5H, m), 2.92-3.02(2H, m), 3.03-3.16(2H, m), 3.51(2H, s), 4.28-4.40(1H, m), 6.90-6.98(1H, m), 7.00-7.10(3H, m), 7.28-7.38(2H, m), 7.39-7.47 (1H, m), 7.79-7.86(1H, m), 8.28-8.60(1H, m)

MS [M+H]⁺=517 colorless powder

EXAMPLE 26

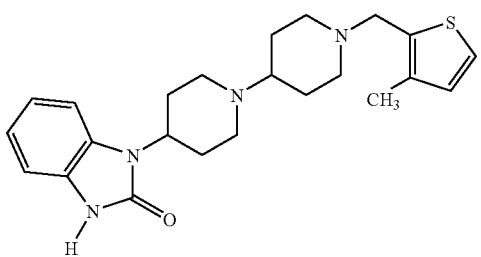

1-[1-[1-[(3-Methyl-2-thienyl)methyl]piperidin-4-yl]piperidin-4-yl]-1,3-dihydro-2H-benzimidazol-2-one ¹H-NMR(300 MHz, CDCl₃) 1.56-1.92(6H, m), 1.98-2.10 (2H, m), 2.19(3H, s), 2.29-2.52(5H, m), 2.98-3.15(4H, m), 3.62(2H, s), 4.28-4.41(1H, m), 6.79(1H, d, J=5.3Hz), 7.00-7.09(3H, m), 7.12(1H, d, J=5.3Hz), 7.28-7.34(1H, m), 8.68-8.84(1H, m)

MS [M+H]⁺=411 colorless powder

EXAMPLE 27

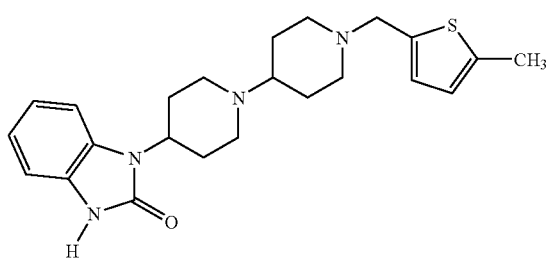

1-[1-[1-[(5-Methyl-2-thienyl)methyl]piperidin-4-yl]piperidin-4yl]-1,3-dihydro-2H-benzimidazol-2-one $^1$H-NMR(300 MHz, CDCl$_3$) 1.50-1.95(6H, m), 1.96-2.12(2H, m), 2.25-2.52(5H, m), 2.45(3H, s), 2.98-3.18(4H, m), 3.64(2H, s), 4.28-4.42(1H, m), 6.55-6.61(1H, m), 6.63-6.70(1H, m), 6.90-7.17(3H, m), 7.20-7.38(1H, m), 8.54-8.70(1H, m)
MS [M+H]$^+$=411
colorless solid

EXAMPLE 28

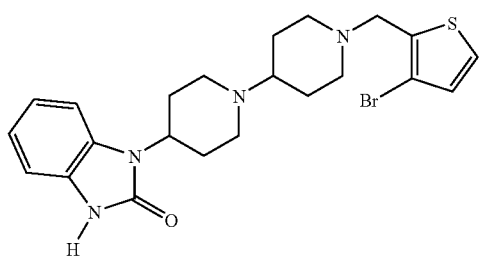

1-[1-[1-[(3-Bromo-2-thienyl)methyl]piperidin-4-yl]piperidin-4-yl]-1,3-dihydro-2H-benzimidazol-2-one $^1$H-NMR(300 MHz, CDCl$_3$) 1.54-1.75(2H, m), 1.77-1.93(4H, m), 2.08-2.20(2H, m), 2.30-2.52(5H, m), 2.98-3.17(4H, m), 3.70(2H, s), 4.28-4.43(1H, m), 6.92(1H, d, J=5.3Hz), 7.00-7.15(3H, m), 7.24(1H, d, J=5.3Hz), 7.27-7.38(1H, m), 8.30-8.80(1H, m)
MS [M+H]$^+$=475, 477
colorless solid

EXAMPLE 29

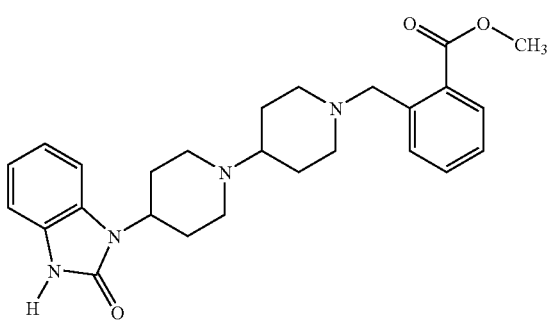

1-[1-[1-[2-(Methoxycarbonyl)benzyl]piperidin-4-yl]piperidin-4yl]-1,3-dihydro-2H-benzimidazol-2-one $^1$H-NMR(300 MHz, CDCl$_3$) 1.50-1.65(2H, m), 1.70-2.10(6H, m), 2.28-2.53(5H, m), 2.80-2.95(2H, m), 3.00-3.18(2H, m), 3.74(2H, s), 3.89(3H, s), 4.28-4.42(1H, m), 7.00-7.13(3H, m), 7.23-7.38(2H, m), 7.39-7.47(2H, m), 7.67-7.72(1H, m), 9.64(1H, brs)
MS [M+H]$^+$=449 colorless solid

EXAMPLE 30

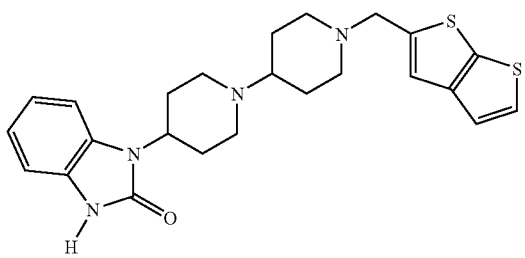

1-[1-[1-[(Thieno[2,3-b]thien-2-yl)methyl]piperidin-4-yl]piperidin-4-yl]-1,3-dihydro-2H-benzimidazol-2-one $^1$H-NMR(300 MHz, CDCl$_3$) 1.58-1.98(6H, m), 2.00-2.12(2H, m), 2.30-2.55(5H, m), 3.00-3.20(4H, m), 3.76(2H, s), 4.28-4.45(1H, m), 7.00-7.24(5H, m), 7.26-7.45(2H, m), 9.40-9.85(1H, m)
MS [M+H]$^+$=453 colorless solid

EXAMPLE 31

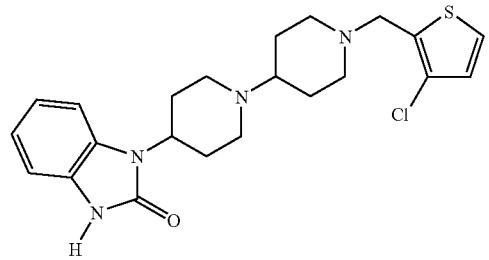

1-[1-[1-[(3-Chloro-2-thienyl)methyl]piperidin-4-yl]piperidin-4-yl]-1,3-dihydro-2H-benzimidazol-2-one A suspension of 29.7 mg of 1-[1-[1-(3-Chloro-2-thenoyl)piperidin-4-yl]piperidin-4-yl]-1,3-dihydro-2H-benzimidazol-2-one and 7 mg of lithium aluminum hydride in 1 ml of THF was stirred at 0° C. for 2 h and then quenched with Na$_2$SO$_4$—10H$_2$O. The mixture was stirred overnight and the insoluble material was removed by filtration. The filtrate was concentrated and purified with PTLC (CHCl$_3$/MeOH/28% aqueous NH$_3$=120/10/1) to give 11.0 mg of the target compound as a colorless solid.

$^1$H-NMR(300 MHz, CDCl$_3$) 1.53-1.95(6H, m), 2.07-2.20(2H, m), 2.28-2.53(5H, m), 2.97-3.17(4H, m), 3.71(2H, s), 4.28-4.43(1H, m), 6.87(1H, d, J=5.3Hz), 6.97-7.12(3H, m), 7.21(1H, d, J=5.3Hz), 7.27-7.38(1H, m), 8.80-9.32(1H, m)
MS [M+H]$^+$=431 colorless foam

EXAMPLE 32

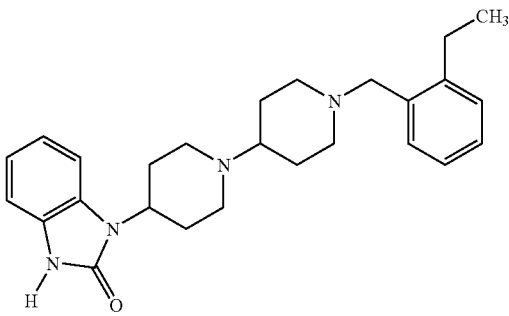

1-[1-[1-(2-Ethylbenzyl)piperidin-4-yl]piperidin-4-yl]-1,3-dihydro-2H-benzimidazol-2-one The title compound was prepared according to the procedure described in Example 31, using 1-[1-[1-(2-ethylbenzyl)piperidin-4-yl]piperidin-4-yl]-1,3-dihydro-2H-benzimidazol-2-one instead of 1-[1-[1-(3-chloro-2-thenoyl)piperidin-4-yl]piperidin-4-yl]-1,3-dihydro-2H-benzimidazol-2-one.

$^1$H-NMR(300 MHz, CDCl$_3$) 1.22(3H, t, J=7.6Hz), 1.50-2.10(8H, m), 2.30-2.55(5H, m), 2.73(2H, q, J=7.6Hz), 2.88-3.15(4H, m), 3.46(2H, s), 4.27-4.42(1H, m), 6.98-7.35(8H, m), 9.90(1H, brs)

MS [M+H]+=419

Colorless amorphous

EXAMPLE 33

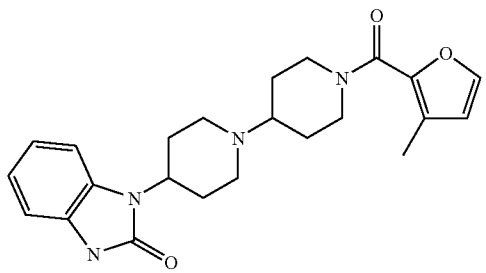

1-[1-[1-(3-Methyl-2-furoyl)piperidin-4-yl]piperidin-4-yl]-1,3-dihydro-2H-benzimidazol-2-one The title compound was prepared according to procedure described in Example 1, using 3-methyl-2-furoic acid instead of 3-thenoic acid.

$^1$H-NMR(300 MHz,CDCl$_3$) 1.42-4.90(19H,m), 2.39(3H, s), 6.34(1H,d,J=1.9Hz), 7.01-7.11(3H,m), 7.23-7.32(1H,m), 8.80-9.12(1H,m)

MS [M+H]+=409

Colorless amorphous

EXAMPLE 34

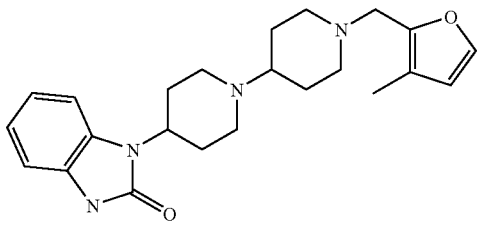

1-[1-[1-(3-Methylfurfuryl)piperidin-4-yl]piperidin-4-yl]-1,3-dihydro-2H-benzimidazol-2-one The title compound was prepared according to the procedure described in Example 31, using 1-[1-[1-(3-methyl-2-furoyl)piperidin-4-yl]piperidin-4-yl]-1,3-dihydro-2H-benzimidazol-2-one.

$^1$H-NMR(300 MHz, CDCl$_3$) 1.55-2.08(8H,m), 2.25(3H, s), 2.30-2.52(5H,m), 2.90-3.16(4H,m), 3.30(2H,s), 4.25-4.40(1H,m), 6.31(1H,d,J=1.8Hz), 6.98-7.10(3H,m), 7.18-7.36(1H,m), 7.24(1H,d,J=1.8Hz), 8.22-9.08(1H,m)

MS [M+H]+=395

Colorless foam

The following examples 35-41 were made in the same manner as described in Example 33 and Example 34 using an appropriate (hetero)arylcarboxylic acid.

EXAMPLE 35

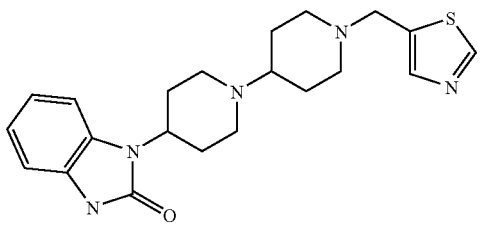

1-[1-[1-(Thiazol-5-ylmethyl)piperidin-4-yl]piperidin-4-yl]-1,3-dihydro-2H-benzimidazol-2-one (prepared from 2-chlorothiazole-5-carboxylic acid)

$^1$H-N(300 MHz, CDCl$_3$) 1.53-1.98(6H,m), 2.00-2.12(2H, m), 2.33-2.55(5H,m), 2.94-3.18(4H,m), 3.76(2H,s), 7.26-4.43(1H,m), 7.00-7.15(3H,m), 7.22-7.36(1H,m), 7.70(1H, s), 8.75(1H,s), 9.09(1H,brs)

MS [M+H]+=398

Slightly yellowish amorphous

EXAMPLE 36

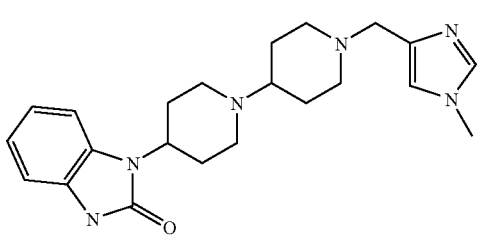

1-[1-[1-[(1-Methyl-1H-imidazol-4-yl)methyl]piperidin-4-yl]piperidin-4-yl]-1,3-dihydro-2H-benzimidazol-2-one ¹H-NMR(300 MHz, CDCl₃) 0.85-2.58(16H,m), 3.04-3.13(1H,m), 3.19(2H,s), 3.67(3H,s), 4.26-4.46(1H,m), 6.90-8.25(7H,m)

MS [M+H]+=395

Colorless solid

EXAMPLE 37

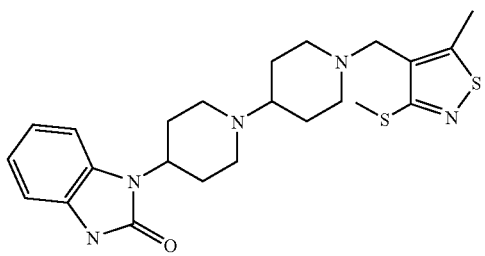

1-[1-[1-[(5-Methyl-3-methylthio-isothiazol-4-yl)methyl]piperidin-4-yl]piperidin-4yl]-1,3-dihydro-2H-benzimidazol-2one ¹H-NMR(300 MHz, CDCl₃) 1.48-1.90(6H,m), 1.93-2.06(2H,m), 2.30-2.75(5H,m), 2.48(3H,s), 2.62(3H,s), 2.84-2.93(2H,m), 3.02-3.13(2H,m), 3.36(2H,s), 4.27-4.40(1H,m), 6.98-7.09(3H,m), 7.27-7.32(1H,m), 8.50-8.77(1H,m)

MS [M+H]+=458

Pale yellow foam

EXAMPLE 38

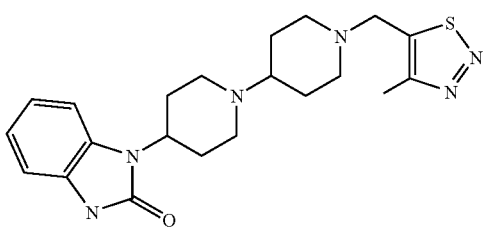

1-[1-[1-[(4-Methyl-1,2,3-thiadiazol-5-yl)methyl]piperidin-4-yl]piperidin-4-yl]-1,3-dihydro-2H-benzimidazol-2-one ¹H-NMR(300 MHz, CDCl₃) 1.56-1.72(2H,m), 1.74-2.00(4H,m), 2.08-2.20(2H,m), 2.23-2.58(5H,m), 2.65(3H,s), 2.94-3.03(2H,m), 3.05-3.18(2H,m), 3.75(2H,s), 4.28-4.42(1H,m), 7.00-7.13(3H,m), 7.27-7.38(1H,m), 9.54(1H,brs)

MS [M+H]+=413

Colorless foam

EXAMPLE 39

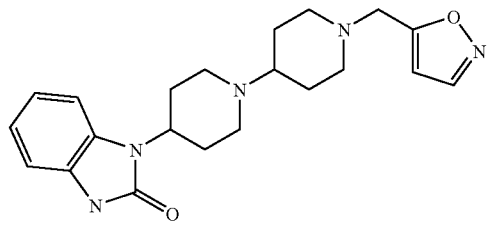

1-[1-[1-[(Isoxazol-5-yl)methyl]piperidin-4-yl]piperidin-4-yl]-1,3-dihydro-2H-benzimidazol-2-one ¹H-NMR(300 MHz,CDCl₃) 1.57-2.00(6H,m), 2.07-2.20(2H,m), 2.30-2.55(5H,m), 2.93-3.15(4H,m), 3.73(2H,s), 4.27-4.41(1H,m), 6.19(1H,s), 6.99-7.12(3H,m), 7.22-7.37(1H,m), 8.21(1H,s), 9.39(1H,brs)

MS [M+H]+=382

Colorless oil

EXAMPLE 40

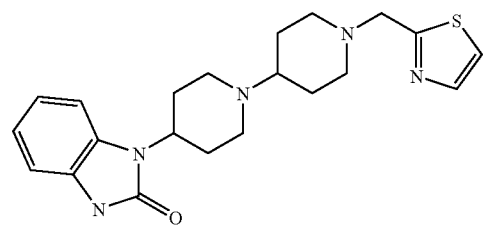

1-[1-[1-[(Thiazol-2-yl)methyl]piperidin-4-yl]piperidin-4-yl]-1,3-dihydro-2H-benzimidazol-2-one ¹H-NMR(300 MHz, CDCl₃) 1.58-2.08(6H,m), 2.14-2.28(2H,m), 2.32-2.55(5H,m), 3.00-3.22(4H,m), 3.87(2H,s), 4.26-4.43(1H,m), 6.98-7.11(3H,m), 7.20-7.38(1H,m), 7.29(1H,d,J=3.3Hz), 7.71(1H,d,J=3.3Hz), 9.08(1H,brs)

MS [M+H]+=398

Colorless foam

EXAMPLE 41

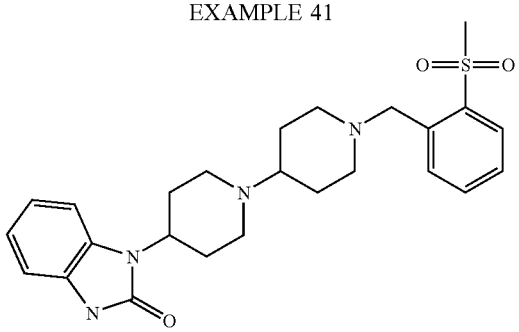

1-[1-[1-(2-Mesylbenzyl)piperidin-4-yl]piperidin-4-yl]-1,3-dihydro-2H-benzimidazol-2-one

MS [M+H]+=469

Colorless amorphous

EXAMPLE 42

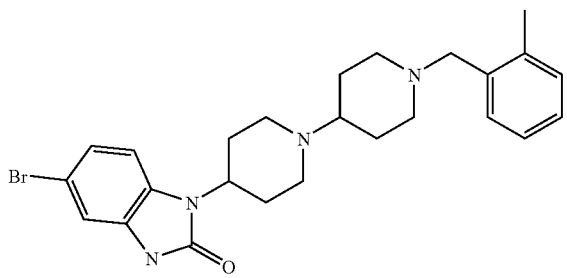

5-Bromo-1-[1-[1-(2-methylbenzyl)piperidin-4-yl]piperidin-4-yl]-1,3-dihydro-2H-benzimidazol-2-one The title compound was prepared according to the procedure described in Example 18, using 5-bromo-1-[1-(piperidin-4-yl)piperidin-4-yl]-1,3-dihydro-2-H-benzimidazol-2one and 2-methylbenzaldehyde.

$^1$H-NMR(300MHz, CDCl$_3$) 1.52-1.90(6H,m), 1.92-2.07 (2H,m), 2.27-2.50(5H,m), 2.36(3H,s), 2.90-3.00(2H,m), 3.02-3.16(2H,m), 3.44(2H,s), 4.27-4.38(1H,m), 7.08-7.32 (7H,m), 9.07(1H,brs)

MS [M+H]+=483/485

Colorless solid

EXAMPLE 43

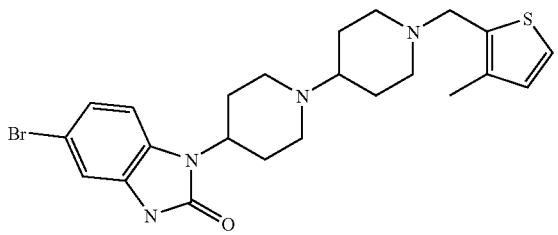

5-Bromo-1-[1-[1-[(3-methyl-2-thienyl)methyl]piperidin-4-yl]piperidin-4-yl]-1,3-dihydro-2H-benzimidazol-2-one The title compound was prepared according to the procedure described in Example 18, using 5-bromo-1-[1-(piperidin-4-yl)piperidin-4-yl]-1,3-dihydro-2H-benzimidazol-2-one and 3-methyl-2-thenaldehyde.

$^1$H-NMR(300 MHz, CDCl$_3$) 1.54-1.90(6H,m), 1.94-2.10 (2H,m), 2.19(3H,s),2.28-2.48(5H,m),2.98-3.16(4H,m),3.62 (2H,s),4.23-4.38(1H,m),6.79(1H,d,J=5.1Hz),7.10-7.32(3H, m),7.13(1H,d,J=5.1Hz),9.02(1H,brs)

MS [M+H]+=489/491

Colorless solid

Functional Assays

Complementary DNA encoding a human m1 receptor gene [cf. *Science.*, 1987:237:527-532] was cloned into an expression vector pcDNA3 (Invitrogen) in which the promoter was modified to human EF-1 alpha promoter, to prepare pEFcDNA3/hm1. The resulting plasmid pEFcDNA3/hm1 was introduced into Chinese hamster ovary cells (CHO) to provide stable hm1/CHO cells that were resistant to selection drugs G418 (Invitrogen).

Hm1/CHO cells were cultured in a DMEM/F12-medium (Invitrogen) overnight to 100% confluence in 96 well culture plate (Packard). Then, hm1/CHO cells were loaded with a calcium indicator Fluo-3 acetoxymethyl ester (Molecular Probes). Compound solutions were added thereto and the intracellular calcium response was measured as a transient increase in fluorescence intensity using FLIPR™ (Molecular Devices).

The Emax value (maximal response) of each compound was calculated relative to carbachol (carbachol=100%). The compounds described herein showed Emax values in the range of about 40% to about 100%.

Effects of the Compound of Example 17, m1 Agonist, on Intraocular Pressure (IOP), Pupil Diameter (PD) in Rabbits and Monkeys Animals Drug-naïve, male Dutch Belted rabbits and female cynomolgus monkeys (*Macaca fascicularis*) were used in this study. Animal care and treatment in this investigation were in compliance with guidelines by the National Institute of Health (NIH) and the Association for Research in Vision and Ophthalmology (ARVO) resolution in the use of animals for research. All experimental procedures had prior approval by the Institutional Animal Care and Use Committee of Merck and Company.

Drug Preparation and Administration

Drug concentrations are expressed in terms of the active ingredient (base). Example 17 was dissolved in physiological saline at 0.1, 0.3, 1.0% for rabbit study and 0.5, 1.0% for monkey studies. Drug or vehicle aliquots (25 ul) were administered topically unilaterally or bilaterally. In unilateral applications, the contralateral eyes received an equal volume of saline. Proparacaine (0.5%) was applied to the cornea prior to tonometry to minimize discomfort. Intraocular pressure (IOP) was recorded using a pneumatic tonometer (Alcon Applanation Pneumatonograph) or equivalent.

Analysis

The results are expressed as the changes in IOP from the basal level measured just prior to administration of drug or vehicle and represent the mean, plus or minus standard deviation. Statistical comparisons were made using the Student's t-test for non-paired data between responses of drug-treated and vehicle-treated animals and for paired data between ipsilateral and contralateral eyes at comparable time intervals. The significance of the date was also determined as the difference from the "t-0" value using Dunnett's "t" test. Asterisks represent a significance level of p<0.05.

Intraocular Pressure Measurement in Rabbits

Male Dutch Belted rabbits weighing 2.5-4.0 kg were maintained on a 12- hour light/dark cycle and rabbit chow. All experiments were performed at the same time of day to minimize variability related to diurnal rhythm. IOP was measured before treatment then Example 17 or vehicle (saline) was instilled (one drop of 25 ul) into one or both eyes and IOP was measured at 30, 60, 120, 180, 240, 300, and 360 minutes after instillation. In some cases, equal number of animals treated bilaterally with vehicle only were evaluated and compared to drug treated animals as parallel controls.

Pupil Diameter (PD) Measurement in Rabbits

Male Dutch Belted rabbits weighing 2.5-4.0 kg were maintained on a 12- hour light/dark cycle and rabbit chow. All experiments were performed at the same time of day to minimize variability related to diurnal rhythm. PD was measured before treatment then Example 17 or vehicle (saline) was instilled (one drop of 25 ul) into one or both eyes and PD was measured at 30, 60, 120, 180, 240, 300, and 360 minutes after instillation. In some cases, equal number of animals treated bilaterally with vehicle only were evaluated and compared to drug treated animals as parallel controls.

Intraocular Pressure Measurements in Monkeys

Unilateral ocular hypertension of the right eye was induced in female cynomolgus monkeys weighing between 2 and 3 kg by photocoagulation of the trabecular meshwork with an argon laser system (Coherent NOVUS 2000, Palo Alto, USA) using the method of Lee at al. (1985). The prolonged increase in intraocular pressure (IOP) results in changes to the optic nerve head that are similar to those found in glaucoma patients.

For IOP measurements, the monkeys were kept in a sitting position in restraint chairs for the duration of the experiment. Animals were lightly anesthetized by the intramuscular injection of ketamine hydrochloride (3-5 mg/kg) approximately five minutes before each IOP measurement and one drop of 0.5% proparacaine was instilled prior to recording IOP. IOP was measured using a pneumatic tonometer (Alcon Applanation Tonometer) or a Digilab pneumatonometer (Bio-Rad Ophthalmic Division, Cambridge, Mass., USA).

IOP was measured before treatment and generally at 30, 60, 124, 180, 300, and 360 minutes after treatment. Baseline values were also obtained at these time points generally two or three days prior to treatment. Treatment consisted of instilling one drop of 25 μl of the compound Example 17 (0.5 and 1.0%) or vehicle (saline). At least one-week washout period was employed before testing on the same animal. The normotensive (contralateral to the hypertensive) eye was treated in an exactly similar manner to the hypertensive eye. IOP measurements for both eyes were compared to the corresponding baseline values at the same time point. Results were expressed as mean plus-or-minus standard deviation in mm Hg.

Pupil Diameter (PD) Measurement in Monkeys

All experiments were performed at the same time of day to minimize variability related to diurnal rhythm. PD was measured with a pupillometer before treatment then Example 17 or vehicle (saline) was instilled (one drop of 25 ul) into one or both eyes and PD was measured at 30, 60, 120, 180, 240, 300, and 360 minutes after instillation. In some cases, equal number of animals treated bilaterally with vehicle only were evaluated and compared to drug treated animals as parallel controls.

Results

Topical unilateral application of the compounds of the claimed invention elicited dose dependent ocular hypotension that was significant when compared to control in Dutch Belted rabbits. In glaucomatous monkey eyes, the compounds of the claimed invention caused significant reduction on IOP. In rabbits and monkeys, the compounds of the claimed invention did not induce ocular hypertension or pupillary constriction (miosis) at any stage of the study.

What is claimed is:

1. A compound of structural formula I:

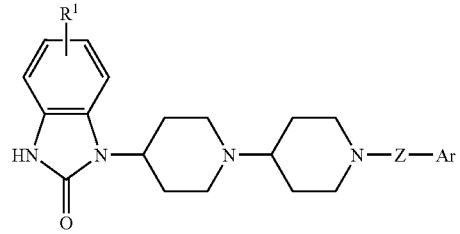

FORMULA I or a pharmaceutically acceptable salt, enantiomer, diastereomer or mixture thereof:
wherein,
$R^1$ represents $R^8$, $(CH_2)_nOR^8$, $COOR, COOR^8$, $(CH_2)_nN(R)(R^8)$, $(CH_2)_nN^+(R)_3$, $(CH_2)_nNRCOR$, $(CH_2)_nN(R^8)CO_2R$, $(CH_2)_nN(R^8)COR$, $(CH_2)_nNRCO_2R$, $SO_2R$, $SO_2N(R)_2$, $(CH_2)_nCON(R)_2$, $CONRR^8$, $CONHC(R)_3$, $COR$, $COR^8$, $CON(R^8)_2$, nitro, or cyano;

Z represents $CH_2$, CO, $CHCO_2R$, or $SO_2$;

Ar represents $(CH_2)_n$ $_{5-11}$ heterocyclyl, $(CH_2)_nC_{5-10}$ heteroaryl, or $(CH_2)_nC_{6-10}$ aryl, said heterocycle, aryl or heteroaryl optionally substituted with 1-3 groups of $R^a$;

$R^a$ represents $C_1-C_6$ alkyl optionally substituted with fluoro, $C_{2-6}$ alkenyl, $C_{2-6}$ alkynyl, F, Cl, I, Br, $(CH_2)_nNR_2$, $(CH_2)_nNRR^8$, $NO_2$, CN, —$CF_3$, —COR, —$COR^8$, —$CONRR^8$, —$CONR_2$, —$(CH_2)_nCOOR$, —$(CH_2)_nNHCOR$, —$(CH_2)_nNHCOR^8$, —$(CH_2)_nNHCOOR$, —$SO_2NR_2$, —$SiR_3$, —$(CH_2)_nOR$, —$(CH_2)_nOR^8$, —$O(CH_2)_nOR$, —$(CH_2)_nO(CH_2)_nOR$, —$S(O)_mR$, —$S(O)_mR^8$, —$C(NH)NH_2$, $R^8$ R represents hydrogen, $C_{1-6}$ alkyl optionally substituted with fluoro, $C_{2-6}$ alkenyl, or $C_{2-6}$ alkynyl;

$R^8$ represents $(CH_2)_nC_{3-8}$ cycloalkyl, $(CH_2)_nC_{5-11}$ heterocycle, $(CH_2)_nC_{5-10}$ heteroaryl, $(CH_2)_nC_{6-10}$ aryl, said heterocycle, aryl or heteroaryl optionally substituted with 1-3 groups of $R^b$;

$R^b$ represents F, Cl, I, Br, or $C_{1-6}$ alkyl n is 0-3 m is 0-2.

2. A compound according to claim 1 wherein Z is $CH_2$.

3. A compound according to claim 1 wherein Z is CO.

4. A compound according to claim 1 wherein Ar is $(CH_2)_nC_{6-10}$ aryl.

5. A compound according to claim 4 wherein Ar is optionally
substituted with 1-2 groups of $R^a$, Z is CO or $CH_2$ and n=0.

6. A compound according to claim 1 wherein Ar is $(CH_2)_nC_{5-10}$ heteroaryl, and all other variables are as originally described.

7. A compound according to claim 6 wherein Ar is optionally substituted with 1-2 groups of $R^a$, Z is CO or $CH_2$ and n=0.

8. A compound which is:
1-[1-[1-(3-Thienoyl)piperidin-4-yl]piperidin-4-yl]-1,3-dihydro-2H-benzimidazol-2-one;
1-[1-[1-(2-Methoxynicotinoyl)piperidin-4-yl]piperidin-4-yl]-1,3-dihydro-2H-benzimidazol-2-one;
1-[1-[1-[2-(Methoxycarbonyl)benzoyl]piperidin-4-yl]piperidin-4-yl]-1,3-dihydro-2H-benzimidazol-2-one;

1-[1-[1-(4-Methoxy-3-thienoyl)piperidin-4-yl]piperidin-4-yl]-1,3-dihydro-2H-benzimidazol-2-one;
1-[1-[1-[(1-Methyl-2-pyrrolyl)carbonyl]piperidin-4-yl]piperidin-4-yl]-1,3-dihydro-2H-benzimidazol-2-one;
1-[1-[1-[(3-Indolyl)carbonyl]piperidin-4-yl]piperidin-4yl]-1,3-dihydro-2H-benzimidazol-2-one;
1-[1-[1-(2-Methylbenzoyl)piperidin-4-yl]piperidin-4-yl]-1,3-dihydro-2H-benzimidazol-2-one;
1-[1-[1-[2-(Methylthio)nicotinoyl]piperidin-4-yl]piperidin-4-yl]-1,3-dihydro-2H-benzimidazol-2-one;
1-[1-[1-[2-(Methylthio)benzoyl]piperidin-4-yl]piperidin-4-yl]-1,3-dihydro-2H-benzimidazol-2-one;
1-[1-[1-[(1,2-Dihydro-1-benzofuran-7-yl)carbonyl]piperidin-4-yl]piperidin-4-yl]-1,3-dihydro-2H-benzimidazol-2-one;
1-[1-[1-(3Chloro-2-thienoyl)piperidin-4-yl]piperidin-4-yl]-1,3-dihydro-2H-benzimidazol-2-one;
1-[1-[1-(2-Ethylbenzoyl)piperidin-4-yl]piperidin-4-yl]-1,3-dihydro-2H-benzimidazol-2-one;
1-[1-[1-[2-(Phenoxymethyl)benzoyl]piperidin-4-yl]piperidin-4-yl]-1,3-dihydro-2H-benzimidazol-2-one;
1-[1-[1-(3-Ethoxy-2-thienoyl)piperidin-4-yl]piperidin-4-yl]-1,3-dihydro-2H-benzimidazol-2-one;
1-[1-[1-(3-Methoxy-2-thienoyl)piperidin-4-yl]piperidin-4yl]-1,3-dihydro-2H-benzimidazol-2-one;
1-[1-[1-(2-Methylbenzyl)piperidin-4-yl]piperidin-4-yl]-1,3-dihydro-2H-benzimidazol-2-one;
1-[1-[1-(2,6-Dimethylbenzyl)piperidin-4-yl]piperidin-4-yl]-1,3-dihydro-2H-benzimidazol-2-one;
1-[1-[1-(2-Chlorobenzyl)piperidin-4-yl]piperidin-4-yl]-1,3-dihydro-2H-benzimidazol-2-one;
1-[1-[1-[2-(Trifluoromethyl)benzyl]piperidin-4-yl]piperidin-4-yl]-1,3-dihydro-2H-benzimidazol-2-one;
1-[1-[1-(2-Thienylmethyl)piperidin-4-yl]piperidin-4-yl]-1,3-dihydro-2H-benzimidazol-2-one;
1-[1-[1-[2-(Methylthio)benzyl]piperidin-4-yl]piperidin-4-yl]-1,3-dihydro-2H-benzimidazol-2-one;
1-[1-[1-(2-Bromobenzyl)piperidin-4-yl]piperidin-4-yl]-1,3-dihydro-2H-benzimidazol-2-one;
1-[1-[1-(2-Hydroxybenzyl)piperidin-4-yl]piperidin-4-yl]-1,3-dihydro-2H-benzimidazol-2-one;
1-[1-[1-(2-Iodobenzyl)piperidin-4-yl]piperidin-4-yl]-1,3-dihydro-2H-benzimidazol-2-one;
1-[1-[1-[(3-Methyl-2-thienyl)methyl]piperidin-4-yl]piperidin-4-yl]-1,3-dihydro-2H-benzimidazol-2-one;
1-[1-[1-[(5-Methyl-2-thienyl)methyl]piperidin-4-yl]piperidin-4-yl]-1,3-dihydro-2H-benzimidazol-2-one;
1-[1-[1-[(3-Bromo-2-thienyl)methyl]piperidin-4-yl]piperidin-4-yl]-1,3-dihydro-2H-benzimidazol-2-one;
1-[1-[1-[2-(Methoxycarbonyl)benzyl]piperidin-4-yl]piperidin-4-yl]-1,3-dihydro-2H-benzimidazol-2-one;
1-[1-[1-[(Thieno[2,3-b]thien-2-yl)methyl]piperidin-4-yl]piperidin-4-yl]-1,3-dihydro-2H-benzimidazol-2-one;
1-[1-[1-[(3-Chloro-2-thienyl)methyl]piperidin-4-yl]piperidin-4-yl]-1,3-dihydro-2H-benzimidazol-2-one;
1-[1-[1-(2-Ethylbenzyl)piperidin-4-yl]piperidin-4-yl]-1,3-dihydro-2H-benzimidazol-2-one;
1-[1-[1-(3-Methyl-2-furoyl)piperidin-4-yl]piperidin-4-yl]-1,3-dihydro-2H-benzimidazol-2-one;
1-[1-[1-(3-Methylfurfuryl)piperidin-4-yl]piperidin-4-yl]-1,3-dihydro-2H-benzimidazol-2-one;
1-[1-[1-(Thiazol-5-ylmethyl)piperidin-4-yl]piperidin-4-yl]-1,3-dihydro-2H-benzimidazol-2-one;
1-[1-[1-[(1-Methyl-1H-imidazol-4-yl)methyl]piperidin-4-yl]piperidin-4-yl]-1,3-dihydro-2H-benzimidazol-2-one;
1-[1-[1-[(5-Methyl-3-methylthio-isothiazol4-yl)methyl]piperidin-4-yl]piperidin-4-yl]-1,3-dihydro-2H-benzimidazol-2-one;
1-[1-[1-[(4Methyl-1,2,3-thiadiazol-5-yl)methyl]piperidin-4-yl]piperidin-4-yl]-1,3-dihydro-2H-benzimidazol-2-one;
1-[1-[1-[(Isoxazol-5-yl)methyl]piperidin-4-yl]piperidin-4-yl]-1,3-dihydro-2H-benzimidazol-2-one;
1-[1-[1-[(Thiazol-2-yl)methyl]piperidin-4-yl]piperidin-4-yl]-1,3-dihydro-2H-benzimidazol-2-one;
1-[1-[1-(2-Methylbenzyl)piperidin-4-yl]piperidin-4-yl]-1,3-dihydro-2H-benzimidazol-2-one;
5-Bromo-1-[1-[1-(2-methylbenzyl)piperidin-4-yl]piperidin-4-yl]-1,3-dihydro-2H-benzimidazol-2-one; or
5-Bromo-1-[1-[1-[(3-methyl-2-thienyl)methyl]piperidin-4-yl]piperdin-4-yl]-1,3-dihydro-2H-benzimidazol-2-one, or a pharmaceutically acceptable salt, enantiomer, diastereomer or mixture thereof.

9. A method for treating ocular hypertension or glaucoma comprising administration to a patient in need of such treatment a therapeutically effective amount of a compound of structural formula I:

FORMULA I

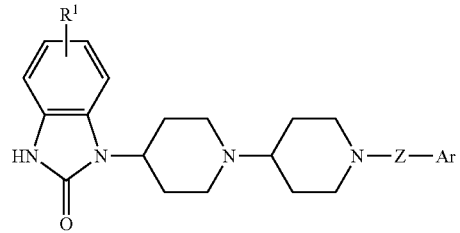

or a pharmaceutically acceptable salt, enantiomer, diastereomer or mixture thereof:

wherein, $R^1$ represents R, $R^8$, $(CH_2)_nOR$, $(CH_2)_nOR^8$, COOR, $COOR^8$, $(CH_2)_nN(R)_2$, $(CH_2)_nN(R)(R^8)$, $(CH_2)_nN^+(R)_3$, $(CH_2)_nNRCOR$, $(CH_2)_nN(R^8)CO_2R$, $(CH_2)_nN(R^8)COR$, $(CH_2)_nNRCO_2R$, $SO_2R$, $SO_2N(R)_2$, $(CH_2)_nCON(R)_2$, $CONRR^8$, $CONHC(R)_3$, COR, $COR^8$, $CON(R^8)_2$, nitro, cyano, or halogen, alkyl or alkoxy optionally substituted with 1-3 groups of $R^a$;

Z represents $CH_2$, CO, $CHCO_2R$, or $SO_2$;

Ar represents $(CH_2)_n$ 5-11 heterocyclyl, $(CH_2)_nC_{5-10}$ heteroaryl, or $(CH_2)_nC_{6-10}$ arly, said heterocycle, aryl or heteroaryl optionally substituted with 1-3 groups of $R^a$;

$R^a$ represents $C_1$-$C_6$ alkyl optionally substituted with fluoro, $C_{2-6}$ alkenyl, $C_{2-6}$ alkynyl, F, Cl, I, Br, $(CH_2)_nNR_2$, $(CH_2)_nNRR^8$, $NO_2$, CN, $-CF_3$, $-COR$, $-COR^8$, $-CONRR^8$, $-CONR_2$, $-(CH_2)_nCOOR$, $-(CH_2)_nNHCOR$, $-(CH_2)_nNHCOR^8$, $-(CH_2)_nNHCOOR$, $-SO_2NR_2$, $-SiR_3$, $-(CH_2)_nOR$, $-(CH_2)_nOR^8$, $-O(CH_2)_nOR$, $-(CH_2)_nO(CH_2)_nOR$, $-S(O)_m$, $-S(O)_mR^8$, $-C(NH)NH_2$, $R^8$;

R represents hydrogen, $C_{1-6}$ alkyl optionally substituted with fluoro, $C_{2-6}$ alkenyl, or $C_{2-6}$ alkynyl;

$R^8$ represents $(CH_2)_nC_{3-8}$ cycloalkyl, $(CH_2)_nC_{5-11}$ heterocyclyl, $(CH_2)_nC_{5-10}$heteroaryl, $(CH_2)_nC_{6-10}$ aryl, said heterocyclyl, aryl or heteroaryl optionally substituted with 1-3 groups of $R^b$;

$R^b$ represents F, Cl, I, Br, or $C_{1-6}$ alkyl;

n is 0-3 and m is 0-2.

10. The method according to claim 9 wherein the compound of formula I is applied as a topical formulation in a solution or suspension.

11. The method according to claim 9 wherein the compound is:

1-[1-[1-(3-Thienoyl)piperidin-4-yl]piperidin-4-yl]-1,3-dihydro-2H-benzimidazol-2-one;

1-[1-[1-(2-Methoxynicotinoyl)piperidin-4-yl]piperidin-4-yl]-1,3-dihydro-2H-benzimidazol-2-one;

1-[1-[1-[2-(Methoxycarbonyl)benzoyl]piperidin-4-yl]piperidin-4-yl]-1,3-dihydro-2H-benzimidazol-2-one;

1-[1-[1-(2-Methoxybenzoyl)piperidin-4-yl]piperidin-4-yl]-1,3-dihydro-2H-benzimidazol-2-one;

1-[1-[1-(4-Methoxy-3-thenoyl)piperidin-4-yl]piperidin-4-yl]-1,3-dihydro-2H-benzimidazol-2-one;

1-[1-[1-[(1-Methyl-2-pyrrolyl)carbonyl]piperidin-4-yl]piperidin-4-yl]-1,3-dihydro-2H-benzimidazol-2-one;

1-[1-[1-[(3-Indolyl)carbonyl]piperidin-4-yl]piperidin-4-yl]-1,3-dihydro-2H-benzimidazol-2-one;

1-[1-[1-(2-Methylbenzoyl)piperidin-4-yl]piperidin-4-yl]-1,3-dihydro-2H-benzimidazol-2-one;

1-[1-[1-[2-(Methylthio)nicotinoyl]piperidin-4-yl]piperidin-4-yl]-1,3-dihydro-2H-benzimidazol-2-one;

1-[1-[1-[2-(Methylthio)benzoyl]piperidin-4-yl]piperidin-4-yl]-1,3-dihydro-2H-benzimidazol-2-one;

1-[1-[1-[(1,2-Dihydro-1-benzofuran-7-yl)carbonyl]piperidin-4-yl]piperidin-4-yl]-1,3-dihydro-2H-benzimidazol-2-one;

1-[1-[1-(3-Chloro-2-thenoyl)piperidin-4-yl]piperidin-4-yl]-1,3-dihydro-2H-benzimidazol-2-one;

1-[1-[1-(2-Ethylbenzoyl)piperidin-4-yl]piperidin-4-yl]-1,3-dihydro-2H-benzimidazol-2-one;

1-[1-[1-[2-(Phenoxymethyl)benzoyl]piperidin-4-yl]piperidin-4-yl]-1,3-dihydro-2H-benzimidazol-2-one;

1-[1-[1-(3-Ethoxy-2-thenoyl)piperidin-4-yl]piperidin-4-yl]-1,3-dihydro-2H-benzimidazol-2-one;

1-[1-[1-(3-Methoxy-2-thenoyl)piperidin-4-yl]piperidin-4-yl]-1,3-dihydro-2H-benzimidazol-2-one;

1-[1-[1-(2-Methylbenzyl)piperidin-4-yl]piperidin-4-yl]-1,3-dihydro-2H-benzimidazol-2-one;

1-[1-[1-(2,6-Dimethylbenzyl)piperidin-4-yl]piperidin-4-yl]-1,3-dihydro-2H-benzimidazol-2-one;

1-[1-[1-(2-Chlorobenzyl)piperidin-4-yl]piperidin-4-yl]-1,3-dihydro-2H-benzimidazol-2-one;

1-[1-[1-[2-(Trifluoromethyl)benzyl]piperidin-4-yl]piperidin-4-yl]-1,3-dihydro-2H-benzimidazol-2-one;

1-[1-[1-[-(2-Thienylmethyl)piperidin-4-yl]piperidin-4-yl]-1,3-dihydro-2H-benzimidazol-2-one;

1-[1-[1-[2-(Methylthio)benzyl]piperidin-4-yl]piperidin-4-yl]-1,3-dihydro-2H-benzimidazol-2-one;

1-[1-[1-(2-Bromobenzyl)piperidin-4-yl]piperidin-4-yl]-1,3-dihydro-2H-benzimidazol-2-one;

1-[1-[1-(2-Hydroxybenzyl)piperidin-4-yl]piperidin-4-yl]-1,3-dihydro-2H-benzimidazol-2-one;

1-[1-[1-(2-Iodobenzyl)piperidin-4-yl]piperidin-4-yl]-1,3-dihydro-2H-benzimidazol-2-one;

1-[1-[1-(3-Methyl-2-thienyl)methyl]piperidin-4-yl]piperidin-4-yl]-1,3-dihydro-2H-benzimidiazol-2-one;

1-[1-[1-[(5-Methyl-2-thienyl)methyl]piperidin-4-yl]piperidin-4-yl]-1,3-dihydro-2H-benzimidazol-2-one;

1-[1-[1-[(3-Bromo-2-thienyl)methyl]piperidin-4-yl]piperidin-4-yl]-1,3-dihydro-2H-benzimidazol-2-one;

1-[1-[1-[2-(Methoxycarbonyl)benzyl]piperidin-4-yl]piperidin-4-yl]-1,3-dihydro-2H-benzimidazol-2-one;

1-[1-[1-[(Thieno[2,3-b]thien-2-yl)methyl]piperidin-4-yl]piperidin-4-yl]-1,3-dihydro-2H-benzimidazol-2-one;

1-[1-[1-[(3-Chloro-2-thienyl)methyl]piperidin-4-yl]piperidin-4-yl]-1,3-dihydro-2H-benzimidazol-2-one;

1-[1-[1-(2-Ethylbenzyl)piperidin-4-yl]piperidin-4-yl]-1,3-dihydro-2H-benzimidazol-2-one;

1-[1-[1-(3-Methyl-2-furoyl)piperidin-4-yl]piperidin-4-yl]-1,3-dihydro-2H-benzimidazol-2-one;

1-[1-[1-(3-Methylfurfuryl)piperidin-4-yl]piperidin-4-yl]-1,3-dihydro-2H-benzimidazol-2-one;

1-[1-[1-(Thiazol-5-ylmethyl)piperidin-4-yl]piperidin-4-yl]-1,3-dihydro-2H-benzimidazol-2-one;

1-[1-[1-[(1-Methyl-1H-imidazol-4-yl)methyl]piperidin-4-yl]piperidin-4-yl]-1,3-dihydro-2H-benzimidazol-2-one;

1-[1-[1-[(5-Methyl-3-methylthio-isothiazol4-yl)methyl]piperidin-4-yl]piperidin-4-yl]-1,3-dihydro-2H-benzimidazol-2-one;

1-[1-[1-[(4-Methyl-1,2,3-thiadiazol-5-yl)methyl]piperidin-4-yl]piperidin-4-yl]-1,3-dihydro-2H-benzimidazol-2-one;

1-[1-[1-[(Isoxazol-5-yl)methyl]piperidin-4-yl]piperidin-4-yl]-1,3-dihydro-2H-benzimidazol-2-one;

1-[1-[1-[(Thiazol-2-yl)methyl]piperidin-4-yl]piperidin-4-yl]-1,3-dihydro-2H-benzimidazol-2-one;

1-[1-[1-(2-Methylbenzyl)piperidin-4-yl]piperidin-4-yl]-1,3-dihydro-2H-benzimidazol-2-one;

5-Bromo-1-[1-[1-(2-methylbenzyl]piperidin-4-yl]piperidin-4-yl]-1,3-dihydro-2H-benzimidazol-2-one; or 5-Bromo-1-[1-[1-[(3-methyl-2-thienyl)methyl]piperidin-4-yl]piperidin-4-yl]-1,3-dihydro-2H-benzimidazol-2-one, or a pharmaceutically acceptable salt, enantiomer, diastereomer or mixture thereof.

12. The method according to claim 10 wherein an active ingredient belonging to the group consisting of: β-adrenergic blocking agent, potassium channel blocker, carbonic anhydrase inhibitor, and a prostaglandin or a prostaglandin derivative is optionally added to the formulation.

13. The method according to claim 12 wherein the β-adrenegic blocking agent is timolol; potassium channel blocker is a maxi-K channel blocker, the carbonic anhydrase inhibitor is dorzolamide, acetazolamide, methazolamide or brinzolamide; the prostaglandin is latanoprost or isopropyl unoprostone, and the prostaglandin derivative is a hypotensive lipid derived from PGF2α prostaglandins.

14. The method according to claim 12 wherein the compound of formula I is applied as a topical formulation in a solution or suspension.

15. The method according to claim 12 in which the topical formulation optionally contains xanthan gum or gellan gum.

* * * * *